(12) United States Patent
Moos

(10) Patent No.: US 12,565,462 B2
(45) Date of Patent: Mar. 3, 2026

(54) BIOMETHANOL PRODUCTION SYSTEM AND METHOD

(71) Applicant: Union Engineering A/S, Fredericia (DK)

(72) Inventor: Kristoffer Moos, Gelsted (DK)

(73) Assignee: Union Engineering A/S, Fredericia (DK)

( * ) Notice: Subject to any disclaimer, the term of this patent is extended or adjusted under 35 U.S.C. 154(b) by 52 days.

(21) Appl. No.: 17/651,384

(22) Filed: Feb. 16, 2022

(65) Prior Publication Data

US 2022/0259123 A1     Aug. 18, 2022

Related U.S. Application Data

(60) Provisional application No. 63/200,129, filed on Feb. 16, 2021.

(51) Int. Cl.
*C07C 29/151* (2006.01)
*B01J 19/24* (2006.01)
*C07C 29/152* (2006.01)

(52) U.S. Cl.
CPC ....... *C07C 29/1512* (2013.01); *B01J 19/2465* (2013.01); *B01J 19/2475* (2013.01); *C07C 29/1518* (2013.01); *C07C 29/152* (2013.01); *B01J 19/248* (2013.01); *B01J 2219/00121* (2013.01); *C01B 2203/0222* (2013.01); *C01B 2203/0415* (2013.01); *C01B 2203/0475* (2013.01); *C01B 2203/061* (2013.01); *C01B 2203/148* (2013.01); *C01B 2203/86* (2013.01)

(58) Field of Classification Search
CPC .............. C07C 29/151; C07C 29/1512; C07C 29/1518; B01J 2219/00006
See application file for complete search history.

(56) References Cited

U.S. PATENT DOCUMENTS

| | | | | | |
|---|---|---|---|---|---|
| 5,736,115 A | * | 4/1998 | Iijima | ....................... | C10L 3/10 |
| | | | | | 423/229 |
| 2019/0308919 A1 | * | 10/2019 | Koss | ..................... | C10K 1/165 |

FOREIGN PATENT DOCUMENTS

| | | |
|---|---|---|
| EP | 0111376 A2 | 6/1984 |
| EP | 2957542 A1 | 12/2015 |
| EP | 4043423 A1 | 8/2022 |
| GB | 1169241 A | 10/1969 |
| WO | 8202547 A1 | 8/1982 |
| WO | 2010080752 A1 | 7/2010 |

OTHER PUBLICATIONS

Extended European Search Report issued by the European Patent Office for European Patent Application No. 22156989.0 issued Jul. 14, 2022, 7 pages.
Communication pursuant to Article 94(3) EPC for European Patent Application No. 22156989.0 issued on Oct. 30, 2025, 7 pages.
Ghosh Shashwata et al., "Biogas to methanol: A comparison of conversion processes involving direct carbon dioxide hydrogenation and via reverse water gas shift reaction", Journal of Cleaner Production, vol. 217, Apr. 1, 2019 (Apr. 1, 2019), pp. 615-626, XP093323499, Amsterdam, NL, ISSN: 0959-6526, DOI: 10.1016/j.jclepro.2019.01.171.

* cited by examiner

*Primary Examiner* — Randy Boyer
(74) *Attorney, Agent, or Firm* — Husch Blackwell LLP

(57) ABSTRACT
A biomethanol production system and method is provided. The system comprises (a) a feed stream comprising methane, water, and carbon dioxide; (b) a reformer reactor capable of reacting the feed stream to form a syngas mixture comprising hydrogen, carbon monoxide, and carbon dioxide; (c) a methanol reactor capable of reacting the syngas mixture to form biomethanol product; (d) a wash column comprising the syngas mixture and the biomethanol product, wherein the biomethanol product is capable of absorbing carbon dioxide from the syngas mixture; and (e) a flash column comprising a vent capable of venting the absorbed carbon dioxide. A method for removing carbon dioxide from a biomethanol production system is also provided.

18 Claims, 5 Drawing Sheets

BIOMETHANOL PRODUCTION SYSTEM AND METHOD

CROSS-REFERENCE TO RELATED APPLICATION

This application claims priority under 35 U.S.C. § 119 to U.S. Provisional Patent Application No. 63/200,129 filed on Feb. 16, 2021, the entire contents of which are incorporated herein by reference.

BACKGROUND

Biomethanol may be produced by first reacting biogas (containing methane, water, and carbon dioxide) in a reformer reactor under high temperature and low-pressure conditions to create a syngas mixture containing hydrogen and carbon monoxide. Then, the syngas mixture is reacted in a methanol reactor under high-pressure and lower temperature conditions to create biomethanol. A known challenge with this system is that biogas contains a surplus of carbon dioxide—more than is needed to yield efficient stoichiometric reactions. In effect, the excess carbon dioxide may reduce the overall system efficiency, leading to reduced biomethanol yields and/or higher operating costs for the system.

Previous attempts have been made to remove excess carbon dioxide from the system by adding hydrogen (such as hydrogen produced from green electric power), which converts the excess carbon dioxide to methanol. However, hydrogen produced using most current methods is expensive. Further, adding hydrogen to the system requires the use of additional equipment and storage tanks, further adding to the system's costs. Thus, the addition of hydrogen is an inefficient solution to the problem of removing excess carbon dioxide from the system.

The art recognizes the need for a method of removing surplus carbon dioxide from the biomethanol production system without requiring additional reactants to be supplied to the system.

SUMMARY

A biomethanol production system is provided. The biomethanol production system comprises (a) a feed stream comprising methane, water, and carbon dioxide; (b) a reformer reactor capable of reacting the feed stream to form a syngas mixture comprising hydrogen, carbon monoxide, and carbon dioxide; (c) a methanol reactor capable of reacting the syngas mixture to form biomethanol product; (d) a wash column comprising the syngas mixture and the biomethanol product, wherein the biomethanol product is capable of absorbing carbon dioxide from the syngas mixture; and (e) a flash column comprising a vent capable of venting the absorbed carbon dioxide.

In some embodiments, the biomethanol production system includes (f) a methanol recycle stream that puts the flash column in fluid communication with the wash column, the methanol recycle stream comprising biomethanol discharged from the flash column; and (g) a $CO_2$-methanol line that puts the wash column in fluid communication with the flash column, the $CO_2$-methanol line comprising the carbon dioxide absorbed in the biomethanol product discharged from the wash column. In further embodiments, the $CO_2$-methanol line comprises at least 100% more carbon dioxide than the methanol recycle stream, based on the total moles of carbon dioxide contained in the respective stream. In some embodiments, the ratio of moles of carbon dioxide in the $CO_2$-methanol line to the moles of carbon dioxide in the methanol recycle stream is from 1.2:1 to 50:1.

In some embodiments, the biomethanol production system includes (h) a wash process stream discharge line that puts the wash column in fluid communication with the methanol reactor, the wash process stream discharge line comprising syngas mixture discharged from the wash column. In further embodiments, wherein the wash process stream discharge line comprises at least 50% less carbon dioxide than the syngas mixture formed in the reformer reactor. In some embodiments, the ratio of moles of carbon dioxide in the syngas mixture formed in the reformer reactor to the moles of carbon dioxide in the wash process stream discharge line is from 80:1 to 35:1.

In some embodiments, the biomethanol production system comprises (a) a feed stream; (b) a reformer reactor configured to react the feed stream to create a syngas mixture; (c) a methanol reactor configured to react the syngas mixture to form a biomethanol product; and (d) a wash column configured to absorb carbon dioxide from the syngas mixture.

In some embodiments, the biomethanol production system may further comprise (e) a device configured to release the absorbed carbon dioxide from the biomethanol stream and vent the absorbed carbon dioxide from the biomethanol production system. Optionally, the device in step (e) may be provided as a flash column comprising a vent capable of venting the absorbed carbon dioxide.

In some embodiments, the biomethanol system further comprises (f) a methanol recycle stream that puts the device in fluid communication with the wash column, the methanol recycle stream comprising biomethanol discharged from the device of step (e); and (g) a $CO_2$-methanol line that puts the wash column in fluid communication with the device, the $CO_2$-methanol line comprising the carbon dioxide absorbed in the biomethanol product discharged from the wash column. In addition, the biomethanol system may further comprise (h) a wash process stream discharge line that puts the wash column in fluid communication with the methanol reactor, the wash process stream discharge line comprising syngas mixture discharged from the wash column.

In some embodiments of the biomethanol production system, the wash column is upstream of the methanol reactor. In other embodiments of the biomethanol production system, the wash column is positioned between a first methanol reactor and a second methanol reactor.

In some embodiments, the biomethanol production system recycles at least two times, or at least three times, or at least ten times, or at least twenty times, or at least thirty times, or at least forty times, or at least forty-five times the amount of methanol that is recovered.

A method for removing carbon dioxide from a biomethanol production system is provided. The method includes (a) reacting biogas in a reformer reactor to form a syngas mixture comprising hydrogen, carbon monoxide, and carbon dioxide; (b) feeding the syngas mixture to a wash column and forming a process stream; (c) feeding the process stream to a first methanol reactor and reacting the process stream to form biomethanol; (d) feeding the biomethanol from the first methanol reactor to a flash column and then to the wash column; (e) absorbing carbon dioxide from the syngas mixture in the wash column with the biomethanol to form a $CO_2$-methanol stream; and (f) recycling the $CO_2$-methanol stream by feeding it to the flash column and releasing the absorbed carbon dioxide.

In some embodiments of the above-described method, the carbon dioxide released in step (f) is vented from the flash column. In some embodiments of the above-described method, a second methanol reactor is positioned between the first methanol reactor and the flash column. In some embodiments, the above-described method excludes at least one of: (i) treating the syngas mixture, the biomethanol, and the CO₂-methanol stream with amines; and (ii) treating the syngas mixture, the biomethanol, and the CO₂-methanol stream with a membrane configured to isolate carbon dioxide from components of the syngas mixture, the biomethanol, and the CO₂-methanol stream.

Another method for removing carbon dioxide from a biomethanol production system is provided. The method includes (a) providing a biogas comprising methane, water, and carbon dioxide; (b) reacting the biogas in a reformer reactor to form a syngas mixture comprising hydrogen, carbon monoxide, and carbon dioxide; (c) feeding the syngas mixture to a wash column and forming a process stream, wherein the process stream contains less carbon dioxide than the syngas mixture; (d) feeding the process stream to a methanol reactor and reacting the contents of the process stream to form biomethanol; (e) feeding the biomethanol from the methanol reactor to a flash column; (f) feeding the biomethanol from the flash column to the wash column; (g) absorbing carbon dioxide from the syngas mixture in the wash column with the biomethanol from the flash column to form a CO₂-methanol stream, wherein the CO₂-methanol stream contains more carbon dioxide than the biomethanol from the flash column; (h) feeding the CO₂-methanol stream to the flash column and releasing the absorbed carbon dioxide from the biomethanol; (i) venting the carbon dioxide from the flash column; and (j) recovering the biomethanol.

In some embodiments, in either of the methods for removing carbon dioxide from a biomethanol production system, the CO₂-methanol stream contains at least 100% more carbon dioxide than the biomethanol from the flash column, based on the total moles of carbon dioxide contained in the respective stream.

In some embodiments, in either of the methods for removing carbon dioxide from a biomethanol production system, the ratio of moles of carbon dioxide in the CO₂-methanol stream to the moles of carbon dioxide in the biomethanol from the flash column is from 10:1 to 50:1.

In some embodiments, either of the methods for removing carbon dioxide from a biomethanol production system excludes treating the syngas mixture, the biomethanol, and the CO₂-methanol stream with amines.

In some embodiments, either of the methods for removing carbon dioxide from a biomethanol production system excludes treating the syngas mixture, the biomethanol, and the CO₂-methanol stream with a membrane configured to isolate carbon dioxide from the respective stream components.

In some embodiments, either of the methods for removing carbon dioxide from a biomethanol production system includes recycling at least two times, or at least three times, or at least ten times, or at least twenty times, or at least thirty times, or at least forty times, or at least forty-five times the amount of methanol that is recovered.

DETAILED DESCRIPTION

Figure 1:
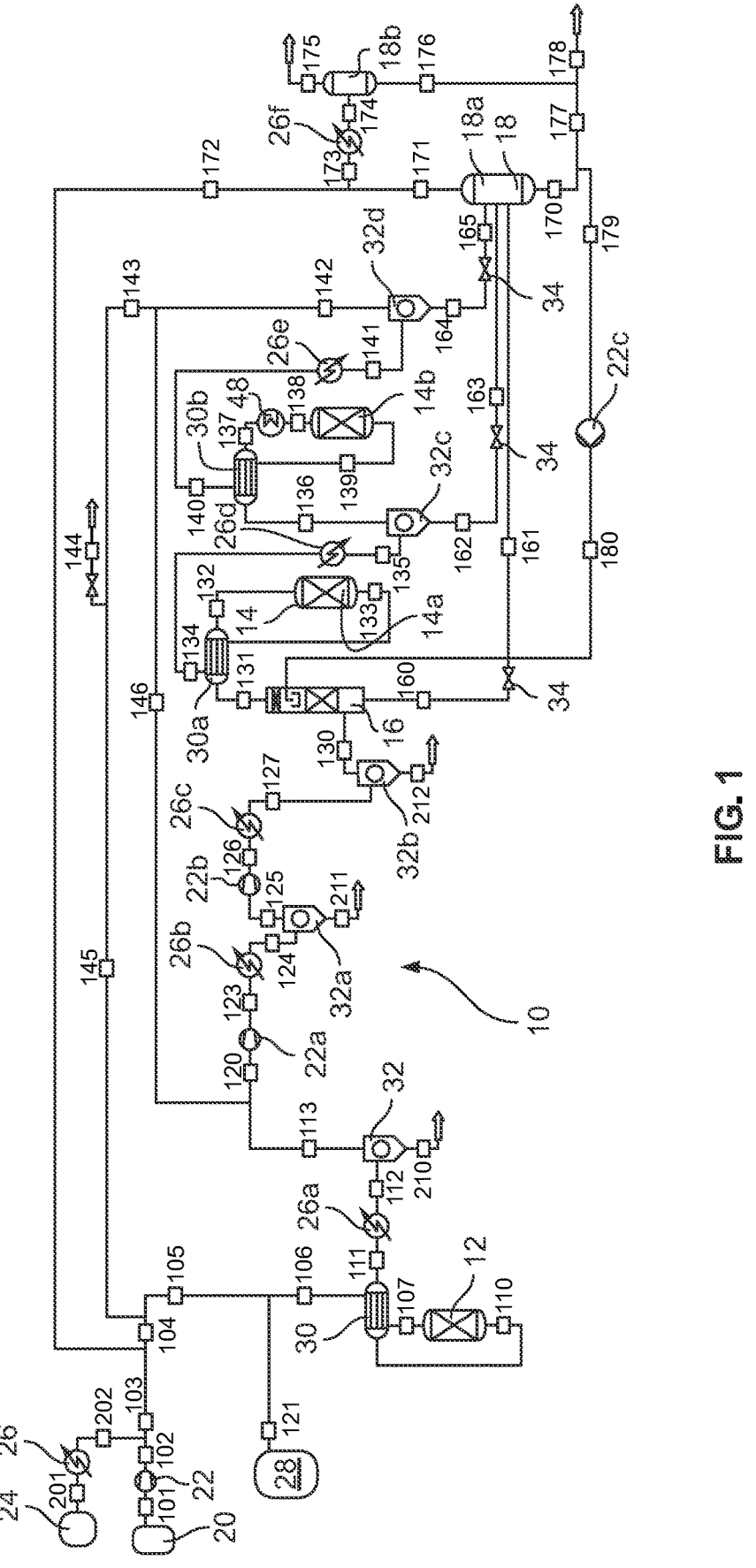
FIG. 1 schematically illustrates a biomethane production system according to one embodiment.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The numerical ranges disclosed herein include all values from, and including, the lower and upper value. For ranges containing explicit values (e.g., a range from 1, or 2, or 3 to 5, or 6, or 7), any subrange between any two explicit values is included (e.g., the range 1-7 above includes subranges 1 to 2; 2 to 6; 5 to 7; 3 to 7; 5 to 6; etc.).

It is understood that the sum of the components in each of the mixtures, compositions, streams, lines, and products disclosed herein yields 100 mole percent.

The term "line" refers to a physical connection between two points. Nonlimiting examples of suitable lines include tubes and pipes. The term "stream" refers to the composition, mixture, or component, contained within and/or passing through a line. It is understood that the terms "line" and "stream" may be used interchangeably herein, such that, for example, the feed line may be referred to herein as the feed stream (and vice versa).

The term "methanol" refers to methyl alcohol, also known as CH₃OH. A nonlimiting example of methanol is biomethanol. The term "biomethanol" refers to a type of methanol that is produced by gasification of organic material (such as biomass, solid waste, coal, or carbon dioxide) to synthesis gas (also known as syngas), followed by methanol synthesis. In some embodiments, biomethanol is produced using biogas. "Biogas" refers to a mixture of gases produced by the breakdown of organic material in the absence of oxygen. Nonlimiting examples of suitable biogas include landfill gas, gas from sewage and/or industrial wastewater treatment, and gas from animal waste. In an embodiment, the biogas is a mixture of gases including methane, carbon dioxide, nitrogen, and hydrogen. While the present application refers to a biomethanol production system and method, it is understood that it may also be used as a methanol production system and method.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Biomethanol Production System

A biomethanol production system is provided. The biomethanol production system comprises (a) a feed stream comprising methane, water, and carbon dioxide; (b) a reformer reactor capable of reacting the feed stream to form a syngas mixture comprising hydrogen, carbon monoxide, and carbon dioxide; (c) a methanol reactor capable of reacting the syngas mixture to form biomethanol product; (d) a wash column comprising the syngas mixture and the biomethanol product, wherein the biomethanol product is capable of absorbing carbon dioxide from the syngas mixture; and (e) a flash column comprising a vent capable of venting the absorbed carbon dioxide. Advantageously, in the above-described system, carbon dioxide is removed without requiring the addition of a separate component feed (e.g., hydrogen or a solvent such as water), or a membrane to remove the carbon dioxide, or pressure swing absorption. Rather, the biomethanol production system may remove carbon dioxide from the process by using at least a portion of the methanol product produced by the biomethanol production system. Removal of carbon dioxide in this manner may increase the efficiency of the system, thereby presenting an opportunity for significant cost savings for the system operator.

Referring now to FIG. 1, a biomethanol production system 10 is shown. In an embodiment, the biomethanol production system 10 includes at least a reformer reactor 12, a methanol reactor 14, a wash column 16, and a flash column 18. The reformer reactor 12 is provided in fluid communication with a gas source 20. The gas source 20 may be a reservoir of a gas mixture. In some embodiments, the gas source 20 may include biogas comprising a variety of components (e.g., methane, carbon dioxide, nitrogen, water, hydrogen, etc.). The biogas may be produced from sources including, but not limited to, as agricultural waste, manure, municipal waste, plant material, sewage, green waste, food waste, anaerobic digester, or combinations thereof, and transferred to the biomethanol production system 10 for reaction. In some embodiments, the biogas undergoes a pre-cleaning step before being transferred to the biomethanol production system 10. During pre-cleaning, the biogas may be filtered using one or more activated carbon filters to remove all, or remove substantially all, contaminants such as $H_2S$ and volatile oxygenated compounds. In an embodiment, the biomethanol production system 10 includes a gas source 20 with a gas mixture containing methane, carbon dioxide, water, and nitrogen.

In some embodiments, the biomethanol production system 10 includes a first gas transport device 22 having a suction side connected to an inlet gas line 101 and a discharge side connected to a feed gas line 102. The feed gas line 102 places the first gas transport device 22 in fluid communication with the reformer reactor 12, and the inlet gas line 101 places the first gas transport device 22 in fluid communication with the gas source 20. In general, the gas transport device 22 may be provided as a mechanical device that adjusts (e.g., increases) the pressure of the gas mixture and may comprise a compressor, a blower, or the like. In some embodiments, the first gas transport device 22 is configured to feed the gas mixture to the reformer reactor 12 at a pressure that ranges between 1.05 bar (105 kPa), or 1.5 bar (150 kPa) to 100 bar (10000 kPa), or more. In other embodiments, the first pressure may range from 1.05 bar (105 kPa) to 5 bar (500 kPa), from 1.5 bar (150 kPa) to 5 bar (500 kPa), or from 1.5 bar (150 kPa) to 35 bar (3500 kPa), or from 1.5 bar (150 kPa) to 25 bar (2500 kPa). In other embodiments, the first pressure may range between about 1.05 bar (105 kPa) to about 100 bar (10000 kPa), or about 1.5 bar (150 kPa) to about 100 bar (10000 kPa), or about 1.5 bar (150 kPa) to about 40 bar (4000 kPa), or about 1.5 bar (150 kPa) to about 35 bar (3500 kPa), or about 1.5 bar (150 kPa) to about 25 bar (2500 kPa), or about 1.5 bar (150 kPa) to about 5 bar (500 kPa).

In some embodiments, the biomethanol production system 10 includes a water source 24 in fluid communication with the reformer reactor 12. The water source 24 may be a reservoir of water or a water mixture containing water and other components. In an embodiment, the water source contains demineralized water. In some embodiments, the biomethanol production system 10 includes a first temperature control device 26 that may be used to adjust the temperature (e.g., heat or cool) of the process streams. For example, the biomethanol production system 10 may include a first temperature control device 26 configured between an inlet water line 201 and a feed water line 202. The feed water line 202 places the first temperature control device 26 in fluid communication with the reformer reactor 12, and the inlet water line 201 places the first temperature control device 26 in fluid communication with the water source 24. Suitable first temperature control devices 26 include devices that heat or cool the process stream, such as heat exchangers or electric heaters.

In some embodiments, the biomethanol production system 10 includes a hydrogen source 28 in fluid communication with the reformer reactor 12. The hydrogen source 28 may be a reservoir of hydrogen or a hydrogen mixture containing hydrogen and other components. In an embodiment, a feed hydrogen line 121 places the hydrogen source 28 in fluid communication with the reformer reactor 12.

The feed gas line 102, the feed water line 202, and the feed hydrogen line 121 each is in fluid communication with the reformer reactor 12. In some embodiments, the feed gas line 102, the feed water line 202, and the feed hydrogen line 121 are combined upstream of the reformer reactor 12 to form a feed stream 106. The feed gas line 102, the feed water line 202, and the feed hydrogen line 121 may be combined simultaneously or at different points before being provided to the reformer reactor 12. The feed stream 106 places the reformer reactor 12 in fluid communication with the gas source 20, the water source 24, and the hydrogen source 28.

The biomethanol production system 10 includes a reformer reactor 12. The reformer reactor has a reformer discharge line 110 that is in fluid communication with the feed stream 106. The reformer reactor 12 places the reformer discharge line 110 in fluid communication with the feed stream 106. The reformer reactor 12 is configured to react the contents of the process stream to form a syngas mixture containing carbon monoxide and hydrogen. In some embodiments, the reformer reactor 12 is set at a temperature of from 500° C., or 600° C., or 700° C., or 800° C., or 850° C. to 900° C., or 950° C., or 1000° C., or 1100° C. In another embodiment, the reformer reactor 12 is set at a temperature of from 500° C. to 1100° C., or from 600° C. to 1000° C., or from 700° C. to 1000° C., or from 800° C. to 900° C., or from 850° C. to 900° C. In some embodiments, the reformer reactor 12 operates at a pressure of greater than 1 bar (a), or greater than 1.5 bar(a). In another embodiment, the reformer reactor 12 operates as a pressure of from 1 bar(a) to 1.8 bar(a), or from 1.5 bar(a) to 1.8 bar(a). When the biomethanol production system 10 includes more than one reformer reactor 12, each reformer reactor may operate at the same conditions (e.g., the same temperature, pressure, pressure drop) or at different conditions.

The reformer reactor 12 is configured to enable a reforming reaction. The reforming reaction is exothermal, and a constant, or substantially constant, heat input is provided to facilitate the reaction while the system is operating. Non-limiting examples of suitable heat inputs include heat from an electrically heated furnace or a fired heater.

The reformer discharge line 110 contains, consists essentially of, or consists of the syngas mixture. In some embodiments, the syngas mixture contains, consists essentially of, or consists of (i) methane, (ii) carbon dioxide, (iii) water, (iv) carbon monoxide, (v) hydrogen, and (vi) nitrogen. In another embodiment, the syngas mixture contains, consists essentially of, or consists of, based on the total mole percentage of the mixture, (i) from greater than 0 mol %, or 0.01 mol %, or 0.05 mol %, or 0.10 mol % to 0.50 mol %, or 1.0 mol %, or 5.0 mol % methane; (ii) from greater than 0 mol %, or 1 mol %, or 3 mol %, or 5 mol % to 10 mol %, or 15 mol %, or 20 mol % carbon dioxide; (iii) from greater than 0 mol %, or 1 mol %, or 5 mol %, or 10 mol % to 15 mol %, or 20 mol %, or 25 mol % water; (iv) from greater than 0 mol %, or 5 mol %, or 10 mol %, or 15 mol %, or 20 mol %, or 25 mol % to 30 mol %, or 35 mol %, or 40 mol % carbon monoxide; (v) from greater than 0 mol %, or 20 mol %, or 30 mol %, or 40 mol %, or 50 mol % to 60 mol %, or 70 mol %, or 75 mol % hydrogen; and (vi) from greater than 0 mol %, or 0.01 mol %, or 0.10 mol % to 0.5 mol %, or 1.0 mol %, or 2.0 mol %, or 5.0 mol %, or 10 mol %, or 15 mol % nitrogen. In another embodiment, the syngas mixture contains, consists essentially of, or consists of, based on the total mole percentage of the mixture, (i) from greater than 0 mol % to 5 mol %, or from 0.01 mol % to 5.0 mol %, or from 0.10 mol %, to 1.0 mol % methane; (ii) from greater than 0 mol % to 20 mol %, or from 1 mol % to 20 mol %, or from 5 mol % to 10 mol % carbon dioxide; (iii) from greater than 0 mol % to 25 mol %, or from 1 mol % to 25 mol %, or from 10 mol % to 15 mol % water; (iv) from greater than 0 mol % to 40 mol %, or from 5 mol % to 40 mol %, or from 20 mol % to 30 mol %, or from 25 mol % to 30 mol % carbon monoxide; (v) from greater than 0 mol % to 75 mol %, or from 20 mol % to 75 mol %, or from 40 mol % to 70 mol %, or from 50 mol % to 60 mol % hydrogen; and (vi) from greater than 0 mol % to 15 mol %, or from greater than 0 mol % to 5 mol %, or from 0.01 mol % to 5.0 mol %, or from 0.10 mol % to 0.5 mol % nitrogen.

In some embodiments, the biomethanol production system 10 includes a first heat exchanger 30 in fluid communication with the reformer reactor 12. In an embodiment, the first heat exchanger 30 places the feed stream 106 in fluid communication with the reformer reactor 12. The first heat exchanger 30 has a first exchange discharge line 107 that is in fluid communication with the feed stream 106 and the reformer reactor 12. In some embodiments, the temperature of the first exchange discharge line 107 is higher than the temperature of the feed stream 106. In an embodiment, the temperature of the first exchange discharge line 107 is at least 200° C., or at least 300° C., or at least 400° C., or at least 500° C., or at least 600° C., or at least 700° C. greater than the temperature of the feed stream 106. In another embodiment, the temperature of the first exchange discharge line 107 is from 100° C. to 1000° C., or from 200° C. to 900° C., or from 300° C. to 900° C., or from 400° C. to 900° C., or from 500° C. to 900° C., or from 600° C. to 900° C., or from 700° C. to 900° C., or from 700° C. to 800° C. greater than the temperature of the feed stream 106. The first heat exchanger 30 has a second exchange discharge line 111 that is in fluid communication with the reformer discharge line 110. In some embodiments, the temperature of the second exchange discharge line 111 is lower than the temperature of the reformer discharge line 110. In an embodiment, the temperature of the second exchange discharge line 111 is at least 100° C., or at least 200° C., or at least 300° C., or at least 400° C., or at least 500° C., or at least 600° C. lower than the temperature of the reformer discharge line 110. In another embodiment, the temperature of the second exchange discharge line 111 is from 100° C. to 1000° C., or from 200° C. to 900° C., or from 300° C. to 800° C., or from 400° C. to 700° C., or from 500° C. to 700° C., or from 600° C. to 700° C. lower than the temperature of the reformer discharge line 110. The first heat exchanger 30 facilitates the use of the temperature difference between the reformer discharge line 110 and the feed stream 106 to cool the reformer discharge line 110 contents and heat the feed stream 106 contents. In other words, thermal energy of the reformer discharge line 110 is transferred to the feed stream 106. This may increase the energy efficiency of the system 10 while helping ensure the reactants are at an appropriate reaction temperature.

In some embodiments, a second temperature control device 26a is provided between the second exchange discharge line 111 and a first separator 32. Suitable second temperature control devices 26a include devices that heat or cool the process stream, such as heat exchangers or electric heaters. In an embodiment, the second temperature control device 26a is configured to cool the process stream. In some embodiments, the second temperature control device 26a is configured to cool the process stream by at least 50° C., or at least 100° C., or at least 150° C., or at least 200° C. In another embodiment, the second temperature control device 26a is configured to cool the process stream by from 25° C. to 300° C., or from 50° C. to 200° C., or from 100° C. to 200° C., or from 150° C. to 200° C.

In some embodiments, the biomethanol production system 10 includes a first separator 32 in fluid communication with the reformer reactor 12. In a further embodiment, the first separator 32 is in fluid communication with the reformer reactor 12 and the methanol reactor 14. Nonlimiting examples of suitable first separators 32 include water separators and gas/liquid separators. In some embodiments, the first separator 32 uses gravitational or centrifugal force to separate the gas phase and the liquid phase of the process stream. The first separator 32 may be fitted with demister or coalescer elements. In an embodiment, the first separator 32 may produce a first liquid stream 210 and a first gas stream 113. The first gas stream 113 may be in fluid communication with a second separator 32a. In some embodiments, the first gas stream 113 contains at least 50% less, or at least 75% less, or at least 80% less, or at least 90% less water than the process stream connected to the feed side of the first separator 32. In another embodiment, the first gas stream 113 contains from 50% to 100%, or from 75% to 99%, or from 80% to 98%, or from 90% to 98% less water than the process stream connected to the feed side of the first separator 32. The first liquid stream 210 may be collected, recycled, and/or discarded.

In addition, in embodiments where at least one separator 32 is provided in the system 10, removal of water may increase the efficiency of the methanol reactor 14 or the system 10 as a whole.

In some embodiments, the biomethanol production system 10 includes a second gas transport device 22a having a suction side connected to the first gas stream 113 and a discharge side connected to a second transport discharge stream 123. The first gas stream 113 places the second gas transport device 22a in fluid communication with the first separator 32, and the second transport discharge stream 123 places the second gas transport device 22a in fluid communication with the second separator 32a. In general, the second gas transport device 22a may be provided as a mechanical device that adjusts (e.g., increases) the pressure of the gas mixture and may comprise a compressor, a blower, or the like. In some embodiments, the second gas transport device 22a is configured to feed the gas mixture to the second separator 32a at a pressure that ranges between 1.0 bar (100 kPa), or 1.5 bar (150 kPa) to 100 bar (10000 kPa), or more. In other embodiments, the second pressure may range between 1.0 bar (100 kPa) to 8 bar (800 kPa), or 1.5 bar (150 kPa) to 8 bar (800 kPa), or 1.5 bar (150 kPa) to 10 bar (1000 kPa), or 5 bar (500 kPa) to 10 bar (1000 kPa). In other embodiments, the first pressure may range between about 1.0 bar (100 kPa) to about 100 bar (10000 kPa), or about 1.5 bar (150 kPa) to about 100 bar (10000 kPa), or about 1.5 bar (150 kPa) to about 40 bar (4000 kPa), or about 1.5 bar (150 kPa) to about 35 bar (3500 kPa), or about 1.5 bar (150 kPa) to about 25 bar (2500 kPa), or about 1.5 bar (150 kPa) to about 8 bar (800 kPa).

In some embodiments, a third temperature control device 26b is configured between the second transport discharge stream 123 and the second separator 32a. Suitable third temperature control devices 26b include devices that heat or cool the process stream, such as heat exchangers or electric heaters. In an embodiment, the third temperature control device 26b is configured to cool the process stream. In some embodiments, the third temperature control device 26b is configured to cool the process stream by at least 50° C., or at least 100° C., or at least 150° C., or at least 200° C., or at least 250° C. In another embodiment, the third temperature control device 26b is configured to cool the process stream by from 25° C. to 300° C., or from 50° C. to 300° C., or from 200° C. to 300° C., or from 250° C. to 300° C.

In some embodiments, the biomethanol production system 10 includes a second separator 32a in fluid communication with the first separator 32. In a further embodiment, the second separator 32a is in fluid communication with the first separator 32 and the methanol reactor 14. Nonlimiting examples of suitable second separators 32a include water separators and gas/liquid separators. In some embodiments, the second separator 32a uses gravitational or centrifugal force to separate the gas phase from the liquid phase of the process stream. The second separator 32a may be fitted with demister or coalescer elements. In an embodiment, the second separator 32a has a second liquid stream 211 and a second gas stream 125. The second gas stream 125 may be in fluid communication with a third separator 32b. In some embodiments, the second gas stream 125 contains at least 20% less, or at least 50% less, or at least 60% less, or at least 70% less water than the process stream connected to the feed side of the second separator 32a. In another embodiment, the second gas stream 125 contains from 20% to 100%, or from 50% to 90%, or from 60% to 90%, or from 70% to 80% less water than the process stream connected to the feed side of the second separator 32a. The second liquid stream 211 may be collected, recycled, and/or discarded.

In some embodiments, the biomethanol production system 10 includes a third gas transport device 22b having a suction side connected to the second gas stream 125 and a discharge side connected to a third transport discharge stream 126. The second gas stream 125 places the third gas transport device 22b in fluid communication with the second separator 32a, and the third transport discharge stream 126 places the third gas transport device 22b in fluid communication with the third separator 32b. In general, the third gas transport device 22b may be provided as a mechanical device that adjusts (e.g., increases) the pressure of the gas mixture and may comprise a compressor, a blower, or the like. In some embodiments, the third gas transport device 22b is configured to feed the gas mixture to the third separator 32b at a pressure that ranges between 1.5 bar (150 kPa) to 100 bar (10000 kPa), or more. In other embodiments, the second pressure may range between 1.5 bar (150 kPa) to 75 bar (7500 kPa), or 1.5 bar (150 kPa) to 50 bar (5000 kPa), or 5 bar (500 kPa) to 50 bar (5000 kPa). In other embodiments, the first pressure may range between about 1.05 bar (105 kPa) to about 100 bar (10000 kPa), or about 1.5 bar (150 kPa) to about 100 bar (10000 kPa), or about 1.5 bar (150 kPa) to about 70 bar (7000 kPa), or about 1.5 bar (150 kPa) to about 60 bar (6000 kPa), or about 10 bar (1000 kPa) to about 60 bar (6000 kPa), or about 10 bar (1000 kPa) to about 50 bar (5000 kPa).

In an alternate embodiment (not shown), the first gas transport device 22, the second gas transport device 22a, and/or the third gas transport device 22b may be stages of a single compressor. For example, the second gas transport device 22a and the third gas transport device 22b may be two stages of a single compressor. In other words, each gas transport device (22, 22a, 22b) may constitute separate single-stage compressors, may constitute separate stages within a single compressor, or a combination thereof.

In some embodiments, a fourth temperature control device 26c is configured between the third transport discharge stream 126 and the third separator 32b. Suitable fourth temperature control devices 26c include devices that heat or cool the process stream, such as heat exchangers or electric heaters. In an embodiment, the fourth temperature control device 26c is configured to cool the process stream. In some embodiments, the fourth temperature control device 26c is configured to cool the process stream by at least 5° C., or at least 10° C., or at least 12° C., or at least 100° C. In another embodiment, the fourth temperature control device 26c is configured to cool the process stream by from 5° C. to 150° C., or from 5° C. to 100° C., or from 5° C. to 50° C., or from 5° C. to 25° C., or from 5° C. to 20° C., or from 5° C. to 15° C., or from 10° C. to 20° C., or from 10° C. to 15° C.

In some embodiments, the biomethanol production system 10 includes a third separator 32b in fluid communication with the second separator 32a. In a further embodiment, the third separator 32b is in fluid communication with the second separator 32a and the methanol reactor 14. Nonlimiting examples of suitable third separators 32b include water separators and gas/liquid separators. In some embodiments, the third separator 32b uses gravitational or centrifugal force to separate the gas phase and the liquid phase of the process stream. The third separator 32b may be fitted with demister or coalescer elements. In an embodiment, the third separator 32b has a third liquid stream 212 and a third gas stream 130.

The third gas stream 130 is in fluid communication with the methanol reactor 14. In some embodiments, the third gas stream 130 contains at least 50% less, or at least 60% less, or at least 80% less, or at least 90% less water than the process stream connected to the feed side of the third separator 32*b*. In another embodiment, the third gas stream 130 contains from 20% to 100%, or from 50% to 99%, or from 60% to 99%, or from 80% to 99%, or from 90% to 99% less water than the process stream connected to the feed side of the third separator 32*b*. The third liquid stream 212 may be collected, recycled, and/or discarded.

The biomethanol production system 10 further includes a wash column 16. The wash column 16 may be configured before (i.e., upstream) of the methanol reactor 14. Alternatively, the wash column 16 may be configured between methanol reactors 14, in embodiments where the biomethanol production system 10 contains at least two methanol reactors 14. Returning to FIG. 1, the wash column 16 is configured upstream of a first methanol reactor 14*a* and a second methanol reactor 14*b*.

The wash column 16 may be a tower containing filling material (structures or random packing) or trays. The wash column 16 facilitates contact between the gas phase and the liquid phase. The wash column 16 may include a demister to remove entrained droplets. The wash column 16 may include one or more beds and may or may not enable redistribution.

The wash column 16 is in fluid communication with the methanol reactor 14, the reformer reactor 12, and the flash column 18. The third gas stream 130 and a methanol recycle stream 180 are fed into the wash column 16. The third gas stream 130 puts the wash column 16 in fluid communication with the third separator 32*b*. The methanol recycle stream 180 puts the wash column 16 in fluid communication with the flash column 18.

In an embodiment, the wash column 16 contains, consists essentially of, or consists of the contents of the third gas stream 130 and the methanol recycle stream 180. In some embodiments, the third gas stream 130 contains, consists essentially of, or consists of (i) methane, (ii) carbon dioxide, (iii) water, (iv) carbon monoxide, (v) hydrogen, (vi) methanol, and (vii) nitrogen. In another embodiment, the third gas stream 130 contains, consists essentially of, or consists of, based on the total mole percentage of the third gas stream 130, (i) from 0.1 mol %, or 0.2 mol %, or 0.3 mol %, or 0.4 mol % to 0.5 mol %, or 0.6 mol %, or 0.8 mol %, or 1.0 mol %, or 5.0 mol % methane; (ii) from 1 mol %, or 2 mol %, or 3 mol %, or 4 mol %, or 5 mol % to 6 mol %, or 8 mol %, or 10 mol %, or 15 mol % carbon dioxide; (iii) from 0 mol %, or greater than 0 mol %, or 0.01 mol % to 0.02 mol %, or 0.05 mol %, or 1.0 mol % water; (iv) from 10 mol %, or 15 mol %, or 20 mol %, or 25 mol %, or 30 mol % to 35 mol %, or 40 mol %, or 45 mol %, or 50 mol % carbon monoxide; (v) from 40 mol %, or 45 mol %, or 50 mol %, or 55 mol %, or 60 mol % to 65 mol %, or 70 mol %, or 75 mol % hydrogen; (vi) from 0 mol %, or greater than 0 mol %, or 0.01 mol %, or 0.05 mol %, or 0.07 mol % to 0.10 mol %, or 0.50 mol %, or 1.0 mol % methanol; and (vii) from greater than 0 mol %, or 0.5 mol %, or 1.0 mol %, or 1.5 mol % to 2.0 mol %, or 5.0 mol %, or 10 mol % nitrogen. In a further embodiment, the third gas stream 130 contains, consists essentially of, or consists of, based on the total mole percentage of the third gas stream 130, (i) from 0.1 mol % to 5.0 mol %, or from 0.1 mol % to 1 mol %, or from 0.2 mol % to 0.8 mol %, or from 0.4 mol % to 0.5 mol % methane; (ii) from 1 mol % to 15 mol %, or from 1 mol % to 10 mol %, or from 3 mol % to 8 mol %, or from 5 mol % to 6 mol % carbon dioxide; (iii) from 0 mol % to 1.0 mol %, or from 0 mol % to 0.05 mol %, or from greater than 0 mol % to 0.05 mol %, or from 0.01 mol % to 0.05 mol %, or from 0.01 mol % to 0.02 mol % water; (iv) from 10 mol % to 50 mol %, or from 15 mol % to 50 mol %, or from 25 mol % to 40 mol %, or from 30 mol % to 35 mol % carbon monoxide; (v) from 40 mol % to 75 mol %, or from 40 mol % to 70 mol %, or from 50 mol % to 75 mol %, or from 60 mol % to 65 mol % hydrogen; (vi) from 0 mol % to 1.0 mol %, or from greater than 0 mol % to 1.0 mol %, or from 0.01 mol % to 1.0 mol %, or from 0.05 mol % to 0.50 mol %, or from 0.07 mol % to 0.10 mol % methanol; and (vii) from greater than 0 mol % to 10 mol %, or from 0.5 mol % to 10 mol %, or from 1.0 mol % to 5.0 mol %, or from 1.5 mol % to 2.0 mol % nitrogen. In some embodiments, the methanol recycle stream 180 contains, consists essentially of, or consists of (i) methane, (ii) carbon dioxide, (iii) water, (iv) carbon monoxide, (v) hydrogen, (vi) methanol, and (vii) nitrogen. In another embodiment, the methanol recycle stream 180 contains, consists essentially of, or consists of, based on the total mole percentage of the methanol recycle stream 180, (i) from 0 mol %, or greater than 0 mol %, or 0.00001 mol % to 0.00005 mol %, or 0.00010 mol % methane; (ii) from 0 mol %, or greater than 0 mol %, or 0.01 mol % to 0.05 mol %, or 0.10 mol % carbon dioxide; (iii) from 0 mol %, or greater than 0 mol %, or 0.01 mol %, or 0.10 mol % to 0.20 mol %, or 0.50 mol %, or 1.0 mol % water; (iv) from 0 mol %, or greater than 0 mol %, or 0.0001 mol % to 0.0005 mol %, or 0.0010 mol % carbon monoxide; (v) from 0 mol %, or greater than 0 mol %, or 0.0001 mol % to 0.0005 mol %, or 0.0010 mol % hydrogen; (vi) from 90 mol %, or 95 mol %, or 98 mol %, or 99 mol % to 99.8 mol %, or 99.9 mol %, or less than 100 mol %, or 100 mol % methanol; and (vii) from 0 mol %, or greater than 0 mol %, or 0.00001 mol % to 0.00005 mol %, or 0.00010 mol %, or 0.00050 mol %, or 25 mol % nitrogen. In some embodiments, the methanol recycle stream 180 contains, consists essentially of, or consists of, based on the total mole percentage of the methanol recycle stream 180, (i) from 0 mol % to 0.00010 mol %, or from greater than 0 mol % to 0.00010 mol %, or from 0.00001 mol % to 0.00005 mol % methane; (ii) from 0 mol % to 0.10 mol %, or from greater than 0 mol % to 0.10 mol %, or from 0.01 mol % to 0.10 mol %, or from 0.01 mol % to 0.05 mol % carbon dioxide; (iii) from 0 mol % to 1.0 mol %, or from greater than 0 mol % to 1.0 mol %, or from 0.01 mol % to 1.0 mol %, or from 0.10 mol % to 0.50 mol %, or from 0.01 mol % to 0.20 mol % water; (iv) from 0 mol % to 0.0010 mol %, or from greater than 0 mol % to 0.0010 mol %, or from 0.0001 mol % to 0.0010 mol %, or from 0.0001 mol % to 0.0005 mol % carbon monoxide; (v) from 0 mol % to 0.0010 mol %, or from greater than 0 mol % to 0.0010 mol %, or from 0.0001 mol % to 0.0010 mol %, or from 0.0001 mol % to 0.0005 mol % hydrogen; (vi) from 90 mol % to 100 mol %, or from 90 mol % to less than 100 mol %, or from 90 mol % to 99.9 mol %, or from 95 mol % to 99.9 mol %, or from 98 mol % to 99.9 mol %, or from 99.0 mol % to 99.9 mol % methanol; and (vii) from 0 mol % to 25 mol %, or from 0 mol % to 0.00050 mol %, or from greater than 0 mol % to 0.00050 mol %, or from 0.00001 mol % to 0.00050 mol %, or from 0.00001 mol % to 0.00005 mol % nitrogen.

Not wishing to be bound by any particular theory, it is believed that the methanol from the methanol recycle stream 180 absorbs carbon dioxide from the third gas stream 130 in the wash column 16. This is advantageous because excess carbon dioxide is removed from the process stream without requiring the addition of a separate component feed (e.g., hydrogen or a solvent such as water), or a membrane to remove the carbon dioxide, or pressure swing absorption. Rather, the present biomethanol production system 10 is configured to remove excess carbon dioxide from the process stream using at least a portion of the methanol product produced by the biomethanol production system 10. This may increase the efficiency of the system 10, thereby presenting an opportunity for significant cost savings for the system operator.

The wash column 16 discharges the process stream via a wash process stream discharge line 131. The methanol containing the absorbed carbon dioxide is discharged from the wash column 16 via a $CO_2$-methanol line 160. The wash process stream discharge line 131 puts the wash column 16 in fluid communication with the first methanol reactor 14a. The $CO_2$-methanol line 160 puts the wash column 16 in fluid communication with the flash column 18. The wash process stream discharge line 131 contains less carbon dioxide than the third gas stream 130. In other words, the process stream contains less carbon dioxide when it is discharged from the wash column 16 relative to the carbon dioxide content of the process stream before it enters the wash column 16. In some embodiments, the wash process stream discharge line 131 contains at least 50% less, or at least 75% less, or at least 80% less, or at least 90% less, or at least 95% less carbon dioxide than the third gas stream 130, based on the total moles of carbon dioxide contained in the respective stream. In another embodiment, the wash process stream discharge line 131 contains from 50% to 100%, or from 50% to less than 100%, or from 75% to 99.9%, or from 80% to 99.9%, or from 90% to 99.9%, or from 95% to 99.9% less carbon dioxide than the third gas stream 130, based on the total moles of carbon dioxide contained in the respective stream. In some embodiments, the ratio of moles of carbon dioxide in the third gas stream 130 to the moles of carbon dioxide in the wash process stream discharge line 131 is from 80:1, or 75:1, or 70:1, or 60:1, or 55:1 to 50:1, or 45:1, or 40:1, or 35:1, or 8:1, or 2:1, or 1.2:1. In another embodiment, the ratio of moles of carbon dioxide in the third gas stream 130 to the moles of carbon dioxide in the wash process stream discharge line 131 is from 80:1 to 1.2:1, or from 80:1 to 2:1, or from 80:1 to 8:1, or from 80:1 to 35:1, or from 80:1 to 45:1, or from 70:1 to 45:1, or from 60:1 to 45:1, or from 55:1 to 50:1. In another embodiment, the ratio of moles of carbon dioxide in the third gas stream 130 to the moles of carbon dioxide in the wash process stream discharge line 131 is from 10:1 to 1.2:1, or from 10:1 to 2:1, or from 10:1 to 5:1, or from 8:1 to 5:1, or from 5:1 to 8:1.

The $CO_2$-methanol line 160 contains more carbon dioxide than the methanol recycle stream 180. In other words, the methanol stream contains more carbon dioxide when it is discharged from the wash column 16 relative to the carbon dioxide content of the methanol stream before it enters the wash column 16. In some embodiments, the $CO_2$-methanol line 160 contains at least 100%, or at least 500%, or at least 1000%, or at least 1500%, or at least 2000% more carbon dioxide than the methanol recycle stream 180, based on the total moles of carbon dioxide contained in the respective stream. In another embodiment, the $CO_2$-methanol line 160 contains from 100% to 5000%, or from 500% to 4000%, or from 1000% to 3000%, or from 2000% to 2500% more carbon dioxide than the methanol recycle stream 180, based on the total moles of carbon dioxide contained in the respective stream. In some embodiments, the ratio of moles of carbon dioxide in the $CO_2$-methanol line 160 to the moles of carbon dioxide in the methanol recycle stream 180 is from 10:1, or 15:1, or 20:1 to 25:1, or 30:1, or 35:1, or 40:1, or 50:1. In another embodiment, the ratio of moles of carbon dioxide in the $CO_2$-methanol line 160 to the moles of carbon dioxide in the methanol recycle stream 180 is from 10:1 to 50:1, or from 15:1 to 40:1, or from 20:1 to 30:1, or from 20:1 to 25:1.

In some embodiments, the biomethanol production system 10 includes a second heat exchanger 30a in fluid communication with the wash column 16 and the first methanol reactor 14a. In an embodiment, the second heat exchanger 30a places the wash process stream discharge line 131 in fluid communication with the first methanol reactor 14a. The second heat exchanger 30a has a third exchange discharge line 132 that is in fluid communication with the wash process stream discharge line 131 and the first methanol reactor 14a. In some embodiments, the temperature of the third exchange discharge line 132 is higher than the temperature of the wash process stream discharge line 131. In an embodiment, the temperature of the third exchange discharge line 132 is at least 100° C., or at least 125° C., or at least 150° C., or at least 160° C. greater than the temperature of the wash process stream discharge line 131. In another embodiment, the temperature of the third exchange discharge line 132 is from 100° C. to 500° C., or from 100° C. to 300° C., or from 100° C. to 200° C., or from 150° C. to 200° C. greater than the temperature of the wash process stream discharge line 131. The second heat exchanger 30a has a fourth exchange discharge line 134 that is in fluid communication with a first methanol reactor discharge line 133. In some embodiments, the temperature of the fourth exchange discharge line 134 is lower than the temperature of the first methanol reactor discharge line 133. In an embodiment, the temperature of the fourth exchange discharge line 134 is at least 50° C., or at least 75° C., or at least 100° C. lower than the temperature of the first methanol reactor discharge line 133. In another embodiment, the temperature of the fourth exchange discharge line 134 is from 50° C. to 500° C., or from 50° C. to 300° C., or from 50° C. to 200° C., or from 100° C. to 200° C., or from 100° C. to 150° C. lower than the temperature of the first methanol reactor discharge line 133. The second heat exchanger 30a facilitates the use of the temperature difference between the wash process stream discharge line 131 and the first methanol reactor discharge line 133 to cool the first methanol reactor discharge line 133 contents and heat the wash process stream discharge line 131 contents. In other words, thermal energy of the first methanol reactor discharge line 133 is transferred to the wash process stream discharge line 131. This may increase the energy efficiency of the system 10 while helping ensure the reactants are at an appropriate reaction temperature.

The biomethanol production system 10 includes a methanol reactor 14. In some embodiments, the biomethanol production system 10 includes at least two methanol reactors 14, or at least four methanol reactors 14. The methanol reactor 14 is configured to react the contents of the process stream (i.e., the syngas mixture) to form a biomethanol product (also referred to herein as "methanol" and "biomethanol"). In some embodiments, the methanol reactor 14 is set at a temperature of from 150° C., or 200° C., or 220° C., or 225° C. to 230° C., or 250° C., or 275° C., or 300° C. In another embodiment, the methanol reactor 14 is set at a temperature of from 150° C. to 300° C., or from 200° C. to 275° C., or from 220° C. to 250° C., or from 220° C. to 230° C. In some embodiments, the methanol reactor 14 is set at a pressure of from 40 bar (4000 kPa), or 45 bar (4500 kPa), or 49 bar (4900 kPa) to 50 bar (5000 kPa), or 55 bar (5500 kPa), or 60 bar (6000 kPa), or 70 bar (7000 kPa). In another embodiment, the methanol reactor 14 is set at a pressure of from 40 bar (4000 kPa) to 70 bar (7000 kPa), or from 45 bar (4500 kPa) to 60 bar (6000 kPa), or from 45 bar (4500 kPa) to 50 bar (5000 kPa). In some embodiments, the pressure of the process stream drops by from 0.01 bar (1 kPa), or 0.02 bar (2 kPa), or 0.05 bar (5 kPa) to 0.06 bar (6 kPa), or 0.07 bar (7 kPa), or 0.10 bar (10 kPa) between entering and discharging from the methanol reactor 14. When the biomethanol production system 10 includes more than one methanol reactor 14, each methanol reactor may operate at the same conditions (e.g., the same temperature, pressure, pressure drop) or at different conditions.

Referring to FIG. 1, the biomethanol production system 10 includes a first methanol reactor 14a and a second methanol reactor 14b. The first methanol reactor 14a and the second methanol reactor 14b are downstream of the wash column 16 and the reformer reactor 12. The first methanol reactor 14a and the second methanol reactor 14b are in fluid communication with each other. The first methanol reactor 14a is in fluid communication with the second heat exchanger 30a, the wash column 16, and the second methanol reactor 14b. The third exchange discharge line 132 and the first methanol reactor discharge line 133 put the first methanol reactor 14a in fluid communication with the second heat exchanger 30a. The first methanol reactor 14a has a feed side that is in fluid communication with the third exchange discharge line 132. The product of the first methanol reactor 14a is discharged via the first methanol reactor discharge line 133. The first methanol reactor discharge line 133 contains more methanol than the third exchange discharge line 132, based on total moles of methanol in the respective streams. In some embodiments, the first methanol reactor discharge line 133 contains at least 500%, or at least 1000%, or at least 1500%, or at least 2000%, or at least 2500% more methanol than the third exchange discharge line 132, based on total moles of methanol in the respective streams. In another embodiment, the first methanol reactor discharge line 133 contains from 500% to 5000%, or from 1000% to 4000%, or from 2000% to 3000% more methanol than the third exchange discharge line 132, based on total moles of methanol in the respective streams. It is understood that in each embodiment the third exchange discharge line 132 may be void of, or substantially void of, methanol.

In an embodiment, the first methanol reactor 14a converts (i) at least 1%, or at least 2%, or at least 5%, or at least 9% of the carbon dioxide and (ii) at least 1%, or at least 2%, or at least 5%, or at least 10%, or at least 20%, or at least 30%, or at least 40%, or at least 41% of the hydrogen, based on the total amount of the respective components flowing through the first methanol reactor 14a (in kg/h), into methanol. In other words, the third exchange discharge line 132 contains, relative to the first methanol reactor discharge line 133, (i) at least 1%, or at least 2%, or at least 5%, or at least 9% more carbon dioxide and (ii) at least 1%, or at least 2%, or at least 5%, or at least 10%, or at least 20%, or at least 30%, or at least 40%, or at least 41% more hydrogen, based on the total amount of the respective components flowing through the respective line (in kg/h). In another embodiment, the first methanol reactor 14a converts (i) from 1%, or 2%, or 5%, or 9% to 10%, or 50%, or 80%, or 100% of the hydrogen and (ii) from 1%, or 2%, or 5%, or 10%, or 20%, or 30%, or 40%, or 41% to 45%, or 50%, or 80%, or 100% of the hydrogen, based on the total amount of the respective components flowing through the first methanol reactor 14a (in kg/h), into methanol.

In an embodiment, the biomethanol production system 10 includes a fifth temperature control device 26d configured between the second heat exchanger 30a and a fourth separator 32c. Suitable fifth temperature control devices 26d include devices that heat or cool the process stream, such as heat exchangers or electric heaters. In an embodiment, the fifth temperature control device 26d is configured to cool the process stream. In some embodiments, the fifth temperature control device 26d is configured to cool the process stream by at least 20° C., or at least 50° C., or at least 75° C., or at least 90° C. In another embodiment, the fifth temperature control device 26d is configured to cool the process stream by from 20° C. to 300° C., or from 50° C. to 300° C., or from 50° C. to 200° C., or from 50° C. to 100° C., or from 90° C. to 100° C.

In some embodiments, the biomethanol production system 10 includes a fourth separator 32c in fluid communication with the fifth temperature control device 26d and the second methanol reactor 14b. In a further embodiment, the fourth separator 32c is in fluid communication with the fifth temperature control device 26d and a third heat exchanger 30b. Nonlimiting examples of suitable fourth separators 32c include water separators and gas/liquid separators. In some embodiments, the fourth separator 32c uses gravitational or centrifugal force to separate the gas phase from the liquid phase of the process stream. The fourth separator 32c may be fitted with demister or coalescer elements. In an embodiment, the fourth separator 32c has a fourth liquid stream 162 and a fourth gas stream 136. The fourth gas stream 136 may be in fluid communication with the third heat exchanger 30b. In some embodiments, the fourth gas stream 136 contains at least 50%, or at least 75%, or at least 80%, or at least 90%, or at least 95%, or at least 97%, or at least 98% less methanol than the process stream connected to the feed side of the fourth separator 32c, based on the total molar content of methanol in the respective streams. In another embodiment, the fourth gas stream 136 contains from 50% to 100%, or from 50% to less than 100%, or from 75% to 99.9%, or from 80% to 99.9%, or from 90% to 99.9%, or from 95% to 99.9% less methanol than the process stream connected to the feed side of the fourth separator 32c, based on the total molar content of methanol in the respective streams. In some embodiments, the fourth liquid stream 162 is in fluid communication with the flash column 18. In an embodiment, the fourth liquid stream 162 contains at least 50 mol %, or at least 75 mol %, or at least 90 mol %, or at least 98 mol %, or at least 99 mol % methanol, based on the total moles of the content of the fourth liquid stream 162. In another embodiment, the fourth liquid stream 162 contains from 50 mol % to 100 mol %, or from 50 mol % to less than 100 mol %, or from 75 mol % to less than 100 mol %, or from 90 mol % to less than 100 mol %, or from 99 mol % to less than 100 mol % methanol, based on the total moles of the content of the fourth liquid stream 162.

In some embodiments, the biomethanol production system 10 includes a third heat exchanger 30b in fluid communication with the fourth separator 32c and the second methanol reactor 14b. In an embodiment, the third heat exchanger 30b places the fourth gas stream 136 in fluid communication with the second methanol reactor 14b. The third heat exchanger 30b has a fifth exchange discharge line 137 that is in fluid communication with the fourth gas stream 136 and the fourth separator 32c. In some embodiments, the temperature of the fifth exchange discharge line 137 is higher than the temperature of the fourth gas stream 136. In an embodiment, the temperature of the fifth exchange discharge line 137 is at least 50° C., or at least 100° C., or at least 150° C., or at least 175° C., or at least 180° C. higher than the temperature of the fourth gas stream 136. In another embodiment, the temperature of the fifth exchange discharge line 137 is from 50° C. to 400° C., or from 100° C. to 300° C., or from 100° C. to 200° C., or from 150° C. to 200° C., or from 175° C. to 190° C. higher than the temperature of the fourth gas stream 136. The third heat exchanger 30b has a sixth exchange discharge line 140 that is in fluid communication with a second methanol reactor discharge line 139. In some embodiments, the temperature of the sixth exchange discharge line 140 is lower than the temperature of the second methanol reactor discharge line 139. In an embodiment, the temperature of the sixth exchange discharge line 140 is at least 50° C., or at least 75° C., or at least 100° C., or at least 120° C. lower than the temperature of the second methanol reactor discharge line 139. In another embodiment, the temperature of the sixth exchange discharge line 140 is from 50° C. to 300° C., or from 75° C. to 200° C., or from 100° C. to 200° C., or from 120° C. to 150° C. lower than the temperature of the second methanol reactor discharge line 139. The third heat exchanger 30b facilitates the use of the temperature difference between the fourth gas stream 136 and the second methanol reactor discharge line 139 to cool the second methanol reactor discharge line 139 contents and heat the fourth gas stream 136 contents. In other words, thermal energy of the second methanol reactor discharge line 139 is transferred to the fourth gas stream 136. This may increase the energy efficiency of the system 10 while helping ensure the reactants are at an appropriate reaction temperature.

In some embodiments, the biomethanol production system 10 includes an electrical heater 48. The electrical heater 48 may be used to facilitate the start-up of the biomethanol production system 10 and turned off when the biomethanol production system 10 is in operation. FIG. 1 depicts an electrical heater 48 in fluid communication with the fifth exchange discharge line 137 and the continuing line 138. However, in alternate embodiments, the heater may be incorporated into one or more of the methanol reactor 14, 14a, 14b.

Referring to FIG. 1, the biomethanol production system 10 includes a second methanol reactor 14b. The second methanol reactor 14b is in fluid communication with the third heat exchanger 30b and a fifth separator 32d. The sixth exchange discharge line 140 and the second methanol reactor discharge line 139 put the second methanol reactor 14b in fluid communication with the fifth separator 32d. The second methanol reactor 14b has a feed side that is in fluid communication with the fifth exchange discharge line 137. The product of the second methanol reactor 14b is discharged via the second methanol reactor discharge line 139. The second methanol reactor discharge line 139 contains more methanol than the fifth exchange discharge line 137, based on total moles of methanol in the respective streams. In some embodiments, the second methanol reactor discharge line 139 contains at least 500%, or at least 1000%, or at least 1500%, or at least 2000%, or at least 4000%, or at least 6000%, or at least 7000% more methanol than the fifth exchange discharge line 137, based on total moles of methanol in the respective streams. In another embodiment, the second methanol reactor discharge line 139 contains from 500% to 10000%, or from 5000% to 10000%, or from 7000% to 8000% more methanol than the fifth exchange discharge line 137, based on total moles of methanol in the respective streams.

In an embodiment, the second methanol reactor 14b converts (i) at least 1%, or at least 2%, or at least 5%, or at least 10% of the carbon dioxide and (ii) at least 1%, or at least 2%, or at least 5%, or at least 10%, or at least 20%, or at least 30%, or at least 35% of the hydrogen, based on the total amount of the respective components flowing through the second methanol reactor 14b (in kg/h), into methanol. In other words, the fifth exchange discharge line 137 contains, relative to the second methanol reactor discharge line 139, (i) at least 1%, or at least 2%, or at least 5%, or at least 10% more carbon dioxide and (ii) at least 1%, or at least 2%, or at least 5%, or at least 10%, or at least 20%, or at least 30%, or at least 35% more hydrogen, based on the total amount of the respective components flowing through the respective line (in kg/h). In another embodiment, the second methanol reactor 14b converts (i) from 1%, or 2%, or 5%, or 10% to 15%, or 50%, or 80%, or 100% of the carbon dioxide and (ii) from 1%, or 2%, or 5%, or 10%, or 20%, or 30%, or 35% to 40%, or 45%, or 50%, or 80%, or 100% of the hydrogen, based on the total amount of the respective components flowing through the second methanol reactor 14b (in kg/h), into methanol.

In some embodiments, the biomethanol production system 10 includes a sixth temperature control device 26e configured between the third heat exchanger 30b and the fifth separator 32d. Suitable sixth temperature control devices 26e include devices that heat or cool the process stream, such as heat exchangers or electric heaters. In an embodiment, the sixth temperature control device 26e is configured to cool the process stream. In some embodiments, the sixth temperature control device 26e is configured to cool the process stream by at least 40° C., or at least 50° C., or at least 75° C., or at least 80° C. In another embodiment, the sixth temperature control device 26e is configured to cool the process stream by from 40° C. to 200° C., or from 50° C. to 150° C., or from 50° C. to 100° C., or from 75° C. to 100° C., or from 80° C. to 90° C.

In some embodiments, the biomethanol production system 10 includes a fifth separator 32d in fluid communication with the sixth temperature control device 26e and the flash column 18. Nonlimiting examples of suitable fifth separators 32d include water separators and gas/liquid separators. In some embodiments, the fifth separator 32d uses gravitational or centrifugal force to separate the gas phase and the liquid phase of the process stream. The second separator 32a may be fitted with demister or coalescer elements. In an embodiment, the fifth separator 32d has a fifth liquid stream 164 and a fifth gas stream 142. The fifth gas stream 142 may be in fluid communication with the feed stream 106 and/or the first gas stream 113. In other words, the fifth gas stream 142 is recycled back into the process stream upstream of the reformer reactor 12 and/or the methanol reactor 14. In some embodiments, the fifth gas stream 142 contains at least 50%, or at least 75%, or at least 80%, or at least 90%, or at least 95%, or at least 97%, or at least 98% less methanol than the process stream connected to the feed side of the fifth separator 32d, based on the total molar content of methanol in the respective streams. In another embodiment, the fifth gas stream 142 contains from 50% to 100%, or from 50% to less than 100%, or from 75% to 99.9%, or from 80% to 99.9%, or from 90% to 99.9%, or from 95% to 99.9% less methanol than the process stream connected to the feed side of the fifth separator 32d, based on the total molar content of methanol in the respective streams. In some embodiments, the fifth liquid stream 164 is in fluid communication with the flash column 18. In an embodiment, the fifth liquid stream 164 contains at least 50 mol %, or at least 75 mol %, or at least 90 mol %, or at least 98 mol %, or at least 99 mol % methanol, based on the total moles of the content of the fifth liquid stream 164. In another embodiment, the fifth liquid stream 164 contains from 50 mol % to 100 mol %, or from 50 mol % to less than 100 mol %, or from 75 mol % to less than 100 mol %, or from 90 mol % to less than 100 mol %, or from 99 mol % to less than 100 mol % methanol, based on the total moles of the content of the fifth liquid stream 164.

In some embodiments, the biomethanol production system 10 includes one or more valves 34 configured to regulate the flowrate in the process stream(s). Regulation of the process stream(s) via the one or more valves 34 may increase the efficiency of the biomethanol production process. A plurality of valves 34 may be provided upstream of the flash column 18, where the control valves 34 are configured to move between an open position, a partially open position, and a closed position. A process measuring device may be provided in one or more of the CO$_2$-methanol line 160, the fourth liquid stream 162, and/or the fifth liquid stream 164. The process measuring device(s) is configured to acquire one or more measured value(s).

The biomethanol production system 10 further includes a controller in electrical communication with the plurality of valves 34 and the process measuring device. The controller may include software stored therein and may be programmed to acquire one or more measured values in the CO$_2$-methanol line 160, the fourth liquid stream 162, and/or the fifth liquid stream 164 using the process measuring devices, and to close or open one or more of the plurality of valves 34 in response to the measured value. In other words, the controller is configured to execute a stored program to: adjust the flowrate and/or pressure of the process stream by moving the plurality of valves 34 between an open and closed position, or a position therebetween. Example valves for use in the biomethanol production system 10 include, without limitation, motor-driven valves, pneumatic values, and manually adjustable valves. The controller may operate autonomously or semi-autonomously, or may read executable software instructions from the memory or a computer-readable medium (e.g., a hard drive, a CD-ROM, flash memory), or may receive instructions via input from a user, or another source logically connected to a computer or device, such as another networked computer or server. For example, the server may be used to control the biomethanol production system 10 via the controller on-site or remotely.

Nonlimiting examples of suitable process measuring devices include pressure measuring devices, flow measuring devices, temperature measuring devices, density measuring devices, viscosity measuring devices, viscosity measuring devices, composition measuring devices, and combinations thereof. Suitable pressure measuring devices include, but are not limited to, pressure transducers, diaphragm bellows, Bourdon tubes, strain gauge, piezoelectric sensors, ionization gauges, and combinations thereof. Suitable flow measuring devices include, but are not limited to, pitot tubes, orifice flow meters, turbine flow meters, electromagnetic field flow meters, neutron bombardment flow meters, ultrasound flow meters, hot-wire anemometry flow meters, and angular momentum flow meters, Coriolis mass flow meters, and combinations thereof. Suitable temperature measuring devices include, but are not limited to, thermocouples, thermistors (e.g., a resistance sensor), oscillating quartz crystal thermometers, radiation pyrometers, and combinations thereof. Suitable density measuring devices include, but are not limited to, vibrating tube densometers, X-ray densometers, differential pressure densometers, and combinations thereof. Suitable viscosity measuring devices include, but are not limited to, capillary viscometers, vibrating ball viscometers, and combinations thereof. Suitable humidity measuring devices include hygrometers that may be configured, for example, to measure precise dew point measurements. Suitable composition measuring devices include, but are not limited to, potentiometry sensors, moisture content sensors (hygrometry or psychrometry), gas chromatography, refractive index device, ultrasound, spectroscopy system (e.g., UV, visible, IR, Mossbauer, Raman, atomic-emission device, X-ray device, electron, ion, nuclear magnetic resonance), polarography device, conductimetry device, mass spectrometry system, differential thermal analysis device, and thermogravity-metric analysis system, and combinations thereof.

The biomethanol production system 10 includes a flash column 18 in fluid communication with the methanol reactor 14 and the reformer reactor 12. In some embodiments, the biomethanol production system 10 includes a plurality of flash columns 18. Referring to FIG. 1, the biomethanol production system 10 contains a first flash column 18a and a second flash column 18b. In some embodiments, the first flash column 18a is in fluid communication with the fifth separator 32d. The first flash column 18a has a feed side in fluid communication with the CO$_2$-methanol line 160. In some embodiments, the first flash column 18a has a feed side in fluid communication with the CO$_2$-methanol line 160, the fourth liquid stream 162, and the fifth liquid stream 164. The first flash column 18a is configured to release the absorbed carbon dioxide from the methanol provided from the CO$_2$-methanol line 160. After release, (i) the carbon dioxide is routed to a vent and released via a first vent stream 171 and (ii) the methanol is routed to the methanol recycle stream 180 and a methanol product recovery stream 178 via a first flash column discharge line 170. In some embodiments, the contents of the first vent stream 171 are routed to (i) the second flash column 18b and/or (ii) to the feed stream 106 via a carbon dioxide recycle line 172. In some embodiments, the first flash column discharge line 170 contains less carbon dioxide than any one of and/or a combination of the CO$_2$-methanol line 160, the fourth liquid stream 162, and the fifth liquid stream 164, based on the total molar content of the respective streams. The first flash column discharge line 170 contains less carbon dioxide than the first vent stream 171, based on the total molar content of the respective streams. In some embodiments, the first vent stream 171 contains at least 100%, or at least 500%, or at least 1000%, or at least 100000%, or at least 150000% more carbon dioxide than the first flash column discharge line 170, based on the total molar content of the respective streams. In an embodiment, the ratio of the molar content of carbon dioxide in the first vent stream 171 to the molar content of carbon dioxide in the first flash column discharge line 170 is from 500:1, or 1000:1, or 1200:1, or 1500:1, or 1600:1 to 1700:1, or 2000:1, or 2500:1, or 3000:1. In another embodiment, the ratio of the molar content of carbon dioxide in the first vent stream 171 to the molar content of carbon dioxide in the first flash column discharge line 170 is from 500:1 to 3000:1, or from 500:1 to 2000:1, or from 1000:1 to 2000:1, or from 1500:1 to 2000:1, or from 1500:1 to 1750:1.

Nonlimiting examples of suitable flash column 18 are disclosed, for example, in U.S. Pat. Nos. 8,652,236, 7,829, 049, and 8,475,566, the entire contents of which are incorporated by reference herein. A nonlimiting example of a suitable flash column 18 is a flash distillation column. Examples of suitable flash columns 18 are columns that contain internal or mass transfer elements such as trays or random or structured packing. The flash column 18 may be a high-pressure flash distillation column, a low-pressure flash distillation column, or a combination thereof. In an alternate embodiment, the flash column 18 may be a flash tank.

In an embodiment, the first vent stream 171 contains, consists essentially or, or consists of (i) methane, (ii) carbon dioxide, (iii) water, (iv) carbon monoxide, (v) hydrogen, (vi) methanol, and (vii) nitrogen. In some embodiments, the first vent stream 171 contains, consists essentially or, or consists of, based on the total molar content of the first vent stream 171, (i) from 0.1 mol %, or 0.5 mol %, or 1.0 mol % to 1.5 mol %, or 2.0 mol %, or 5.0 mol % methane; (ii) from 40 mol %, or 45 mol %, or 50 mol % to 55 mol %, or 60 mol %, or 75 mol %, or 80 mol % carbon dioxide; (iii) from 0 mol %, or greater than 0 mol %, or 0.01 mol % to 0.02 mol %, or 0.05 mol %, or 0.10 mol % water; (iv) from 5 mol %, or 10 mol %, or 15 mol % to 16 mol %, or 20 mol %, or 25 mol % carbon monoxide; (v) from 5 mol %, or 10 mol %, or 13 mol % to 15 mol %, or 20 mol %, or 25 mol % hydrogen; (vi) from 5 mol %, or 10 mol %, or 15 mol % to 20 mol %, or 25 mol %, or 30 mol % methanol; and (vii) from 0.5 mol %, or 1.0 mol % to 2.0 mol %, or 5.0 mol % nitrogen. In another embodiment, the first vent stream 171 contains, consists essentially or, or consists of, based on the total molar content of the first vent stream 171, (i) from 0.1 mol % to 5.0 mol %, or from 1.0 mol % to 2.0 mol %, or from 1.5 mol % to 2.0 mol % methane; (ii) from 40 mol % to 80 mol %, or from 40 mol % to 60 mol %, or from 50 mol % to 60 mol %, or from 50 mol % to 55 mol % carbon dioxide; (iii) from 0 mol % to 0.10 mol %, or from greater than 0 mol % to 0.01 mol %, or from 0.01 mol % to 0.10 mol %, or from 0.01 mol % to 0.02 mol % water; (iv) from 5 mol % to 25 mol %, or from 10 mol % to 20 mol %, or from 15 mol % to 20 mol %, or from 15 mol % to 16 mol % carbon monoxide; (v) from 5 mol % to 25 mol %, or from 10 mol % to 20 mol %, or from 10 mol % to 15 mol %, or from 13 mol % to 15 mol % hydrogen; (vi) from 5 mol % to 30 mol %, or from 1 mol % to 25 mol %, or from 10 mol % to 20 mol %, or from 15 mol % to 20 mol % methanol; and (vii) from 0.5 mol % to 5.0 mol %, or from 1.0 mol % to 2.0 mol % nitrogen.

In some embodiments, the first flash column discharge line 170 contains, consists essentially of, or consists of, (i) methane, (ii) carbon dioxide, (iii) water, (iv) carbon monoxide, (v) hydrogen, (vi) methanol, and (vii) nitrogen. In an embodiment, the first flash column discharge line 170 contains, consists essentially of, or consists of, based on the total molar content of the first flash column discharge line 170, (i) from 0 mol %, or greater than 0 mol %, or 0.00001 mol % to 0.00005 mol %, or 0.0001 mol %, or 0.001 mol % methane; (ii) from 0.01 mol %, or 0.02 mol %, or 0.03 mol % to 0.05 mol %, or 0.10 mol %, or 0.50 mol % carbon dioxide; (iii) from 0 mol %, or greater than 0 mol %, or 0.01 mol %, or 0.10 mol % to 0.20 mol %, or 0.50 mol %, or 1.0 mol % water; (iv) from 0 mol %, or greater than 0 mol %, or 0.0001 mol % to 0.0003 mol %, or 0.001 mol %, or 0.01 mol % carbon monoxide; (v) from 0 mol %, or greater than 0 mol %, or 0.0001 mol %, or 0.0002 mol % to 0.0003 mol %, or 0.0005 mol %, or 0.001 mol %, or 0.01 mol % hydrogen; (vi) from 60 mol %, or 70 mol %, or 80 mol %, or 90 mol %, or 95 mol %, or 97 mol %, or 98 mol %, or 99 mol % to 99.5 mol %, or 99.9 mol %, or less than 100 mol % methanol; and (vii) from 0 mol %, or greater than 0 mol %, or 0.00001 mol % to 0.00002 mol %, or 0.0001 mol %, or 0.001 mol % nitrogen. In another embodiment, the first flash column discharge line 170 contains, consists essentially of, or consists of, based on the total molar content of the first flash column discharge line 170, (i) from 0 mol % to 0.001 mol %, or from greater than 0 mol % to 0.001 mol %, or from 0.00001 mol % to 0.0001 mol %, or from 0.00001 mol % to 0.00005 mol % methane; (ii) from 0.01 mol % to 0.50 mol %, or from 0.02 mol % to 0.10 mol %, or from 0.03 mol % to 0.05 mol % carbon dioxide; (iii) from 0 mol % to 1.0 mol %, or from greater than 0 mol % to 1.0 mol %, or from 0.01 mol % to 1.0 mol %, or from 0.10 mol % to 0.20 mol % water; (iv) from 0 mol % to 0.01 mol %, or from greater than 0 mol % to 0.01 mol %, or from 0.00001 mol % to 0.001 mol %, or from 0.0001 mol % to 0.0003 mol % carbon monoxide; (v) from 0 mol % to 0.01 mol %, or from greater than 0 mol % to 0.01 mol %, or from 0.0001 mol % to 0.001 mol %, or from 0.0002 mol % to 0.0003 mol % hydrogen; (vi) from 60 mol % to less than 100 mol %, or from 60 mol % to 99.9 mol %, or from 80 mol % to 99.9 mol %, or from 90 mol % to 99.9 mol %, or from 95 mol % to 99.9 mol %, or from 98 mol % to 99.9 mol %, or from 99 mol % to less than 100 mol % methanol; and (vii) from 0 mol % to 0.001 mol %, or from greater than 0 mol % to 0.001 mol %, or from 0.00001 mol % to 0.0001 mol %, or from 0.00001 mol % to 0.00002 mol % nitrogen.

In some embodiments, the biomethanol production system 10 includes a liquid transport device 22c having a suction side connected to a second inlet liquid line 179 and a discharge side connected to the methanol recycle stream 180. The first flash column discharge line 170 and the second inlet liquid line 179 place the liquid transport device 22c in fluid communication with the first flash column 18a. The methanol recycle stream 180 places the liquid transport device 22c in fluid communication with the wash column 16. In general, the liquid transport device 22c may be provided as a mechanical device that adjusts (e.g., increases) the pressure of the liquid (and/or gas) mixture and may comprise a pump or the like. In some embodiments, the liquid transport device 22c is configured to feed the gas mixture to the wash column at a pressure that ranges from 20 bar (2000 kPa), or 30 bar (3000 kPa), or 40 bar (4000 kPa), or 50 bar (5000 kPa) to 55 bar (5500 kPa), or 60 bar (6000 kPa), or 70 bar (7000 kPa), or 80 bar (8000 kPa). In other embodiments, the liquid transport device 22c is configured to feed the gas mixture to the wash column at a pressure that ranges from 20 bar (2000 kPa) to 80 bar (8000 kPa), or from 40 bar (4000 kPa) to 60 bar (6000 kPa), or from 50 bar (5000 kPa) to 60 bar (6000 kPa).

In some embodiments, the biomethanol production system 10 includes a seventh temperature control device 26f provided between the first flash column 18a and the second flash column 18b. Suitable seventh temperature control devices 26f include devices that heat or cool the vent stream, such as heat exchangers or electric heaters. In an embodiment, the seventh temperature control device 26f is configured to cool the vent stream. In some embodiments, the seventh temperature control device 26f is configured to cool the vent stream by at least 10° C., or at least 20° C., or at least 25° C., or at least 30° C. In another embodiment, the seventh temperature control device 26f is configured to cool the vent stream by from 10° C. to 100° C., or from 10° C. to 50° C., or from 20° C. to 40° C., or from 30° C. to 40° C.

In some embodiments, the biomethanol production system 10 includes a second flash column 18b in fluid communication with the first flash column 18a. The second flask column 18b has a feed side in fluid communication with the first vent stream 171. The second flash column 18b is configured to remove the liquified/condensed methanol from the gas stream from the first vent stream 171. After removal, (i) the carbon dioxide is routed to a vent and released via a second vent stream 175, and (ii) the methanol is route to the methanol product recovery stream 178 via a second flash column discharge line 176. The contents of the second vent stream 175 may be discarded, collected, and/or recycled. In some embodiments, the second flash column discharge line 176 contains less carbon dioxide than the first vent stream 171, based on the total molar content of the respective streams. The second flash column discharge line 176 contains less carbon dioxide than the second vent stream 175, based on the total molar content of the respective streams. In some embodiments, the second vent stream 175 contains at least 100%, or at least 500%, or at least 1000%, or at least 2000%, or at least 3000%, or at least 3500% more carbon dioxide than the second flash column discharge line 176, based on the total molar content of the respective streams. In an embodiment, the ratio of the molar content of carbon dioxide in the second vent stream 175 to the molar content of carbon dioxide in the second flash column discharge line 176 is from 30:1, or 40:1, or 50:1, or 55:1, or 58:1 to 60:1, or 65:1, or 70:1, or 80:1, or 100:1. In another embodiment, the ratio of the molar content of carbon dioxide in the second vent stream 175 to the molar content of carbon dioxide in the second flash column discharge line 176 is from 30:1 to 100;1, or from 50:1 to 80:1, or from 55:1 to 70:1, or from 55:1 to 65:1, or from 58:1 to 60:1.

In an embodiment, the second vent stream 175 contains, consists essentially or, or consists of (i) methane, (ii) carbon dioxide, (iii) water, (iv) carbon monoxide, (v) hydrogen, (vi) methanol, and (vii) nitrogen. In some embodiments, the second vent stream 175 contains, consists essentially or, or consists of, based on the total molar content of the second vent stream 175, (i) from 0.01 mol %, or 0.1 mol %, or 0.5 mol %, or 1.0 mol % to 1.5 mol %, or 2.0 mol %, or 5.0 mol % methane; (ii) from 30 mol %, or 40 mol %, or 45 mol %, or 50 mol %, or 55 mol %, or 59 mol % to 60 mol %, or 65 mol %, or 70 mol %, or 75 mol %, or 80 mol %, or 90 mol % carbon dioxide; (iii) from 0 mol %, or greater than 0 mol %, or 0.001 mol % to 0.002 mol %, or 0.01 mol %, or 0.10 mol % water; (iv) from 5 mol %, or 10 mol %, or 15 mol %, or 17 mol % to 20 mol %, or 25 mol %, or 30 mol %, or 35 mol %, or 40 mol % carbon monoxide; (v) from 5 mol %, or 10 mol %, or 15 mol %, or 13 mol % to 15 mol %, or 20 mol %, or 25 mol %, or 30 mol %, or 40 mol % hydrogen; (vi) from 0.01 mol %, or 1.0 mol %, or 2.0 mol %, or 4.0 mol % to 5.0 mol %, or 8.0 mol %, or 10 mol %, or 15 mol %, or 20 mol % methanol; and (vii) from 0.01 mol %, or 0.10 mol %, or 0.50 mol %, or 1.0 mol % to 1.5 mol %, or 2.0 mol %, or 5.0 mol %, or 10 mol %, or 15 mol %, or 25 mol % nitrogen. In another embodiment, the second vent stream 175 contains, consists essentially or, or consists of, based on the total molar content of the second vent stream 175, (i) from 0.01 mol % to 5.0 mol %, or from 0.1 mol % to 2.0 mol %, or from 1.0 mol % to 2.0 mol %, or from 1.0 mol % to 1.5 mol % methane; (ii) from 30 mol % to 90 mol %, or from 40 mol % to 70 mol %, or from 50 mol % to 60 mol %, or from 55 mol % to 60 mol % carbon dioxide; (iii) from 0 mol % to 0.10 mol %, or from greater than 0 mol % to 0.10 mol %, or from 0.001 mol % to 0.01 mol %, or from 0.001 mol % to 0.002 mol % water; (vi) from 5 mol % to 40 mol %, or from 10 mol % to 30 mol %, or from 15 mol % to 25 mol %, or from 17 mol % to 20 mol % carbon monoxide; (v) from 5 mol % to 40 mol %, or from 10 mol % to 30 mol %, or from 15 mol % to 20 mol %, or from 13 mol % to 15 mol % hydrogen; (vi) from 0.01 mol % to 20 mol %, or from 1.0 mol % to 10 mol %, or from 2.0 mol % to 8.0 mol %, or from 4.0 mol % to 5.0 mol % methanol; and (vii) from 0.01 mol % to 25 mol %, or from 0.01 mol % to 5.0 mol %, or from 0.10 mol % to 2.0 mol %, or from 0.50 mol % to 1.5 mol %, or from 1.0 mol % to 1.5 mol % nitrogen.

In some embodiments, the second flash column discharge line 176 contains, consists essentially or, or consists of (i) methane, (ii) carbon dioxide, (iii) water, (iv) carbon monoxide, (v) hydrogen, (vi) methanol, and (vii) nitrogen. In some embodiments, the second flash column discharge line 176 contains, consists essentially or, or consists of, based on the total molar content of the second flash column discharge line 176, (i) from 0 mol %, or greater than 0 mol %, or 0.00001 mol %, or 0.00005 mol % to 0.0001 mol %, or 0.001 mol % methane; (ii) from 0 mol %, or greater than 0 mol %, or 0.1 mol %, or 0.5 mol %, or 1.0 mol % to 2.0 mol %, or 5.0 mol %, or 10 mol % carbon dioxide; (iii) from 0 mol %, or greater than 0 mol %, or 0.01 mol %, or 0.05 mol % to 0.10 mol %, or 0.50 mol %, or 1.0 mol %, or 5.0 mol % water; (iv) from 0 mol %, or greater than 0 mol %, or 0.0001 mol % to 0.0005 mol %, or 0.001 mol %, or 0.01 mol % carbon monoxide; (v) from 0 mol %, or greater than 0 mol %, or 0.0001 mol % to 0.0005 mol %, or 0.001 mol %, or 0.01 mol % hydrogen; (vi) from 50 mol %, or 60 mol %, or 70 mol %, or 80 mol %, or 90 mol %, or 95 mol %, or 98 mol % to 99 mol %, or 99.5 mol %, or 99.9 mol %, or less than 100 mol %, or 100 mol % methanol; and (vii) from 0 mol %, or greater than 0 mol %, or 0.00001 mol % to 0.00005 mol %, or 0.0001 mol %, or 0.001 mol % nitrogen. In another embodiment, the second flash column discharge line 176 contains, consists essentially or, or consists of, based on the total molar content of the second flash column discharge line 176, (i) from 0 mol % to 0.001 mol %, or from greater than 0 mol % to 0.001 mol %, or 0.00001 mol % to 0.001 mol %, or from 0.00005 mol % to 0.0001 mol % methane; (ii) from 0 mol % to 10 mol %, or from greater than 0 mol % to 10 mol %, or from 0.01 mol % to 10 mol %, or from 1.0 mol % to 2.0 mol % carbon dioxide; (iii) from 0 mol % to 5 mol %, or from greater than 0 mol % to 5 mol %, or from 0.01 mol % to 5 mol %, or from 0.05 mol % to 0.10 mol % water; (iv) from 0 mol % to 0.01 mol %, or from greater than 0 mol % to 0.01 mol %, or from 0.0001 mol % to 0.01 mol %, or from 0.0001 mol % to 0.0005 mol % carbon monoxide; (v) from 0 mol % to 0.01 mol %, or from greater than 0 mol % to 0.01 mol %, or from 0.0001 mol % to 0.0005 mol % hydrogen; (vi) from 50 mol % to 100 mol %, or from 50 mol % to less than 100 mol %, or from 50 mol % to 99.9 mol %, or from 70 mol % to 99.9 mol %, or from 90 mol % to 99.9 mol %, or from 98 mol % to 99.9 mol % methanol; and (vii) from 0 mol % to 0.001 mol %, or from greater than 0 mol % to 0.001 mol %, or from 0.00001 mol % to 0.001 mol %, or from 0.00001 mol % to 0.00005 mol % nitrogen.

In some embodiments, the methanol product recovery stream 178 is in fluid communication with the first flash column discharge line 170 and the second flash column discharge line 176. The contents of the methanol product recovery stream 178 may be recovered, recycled, or further filtered (e.g., by passing the contents through another flash column 18 and/or separator).

In some embodiments, the biomethanol production system 10 recycles at least twice the amount of methanol that is recovered. In other words, the methanol recycle stream 180 contains at least two times, or at least three times, or at least ten times, or at least twenty times, or at least thirty times, or at least forty times, or at least forty-five times the amount of methanol (in kg/h) than the methanol product recovery stream 178. In some embodiments, the methanol recycle stream 180 contains from two times (2×), or three times (3×), or ten times (10×), or twenty times (20×), or thirty times (30×), or forty times (40×), or forty-five times (45×) to fifty times (50×), or seventy-five times (75×), or one hundred times (100×) the amount of methanol (in kg/h) than the methanol product recovery stream 178. In another embodiment, the methanol recycle stream 180 contains from 2× to 100×, or from 10× to 100×, or from 20× to 100×, or from 30× to 100×, or from 40× to 100×, or from 45× to 100×, or from 40× to 75×, or from 40× to 50×, or from 45× to 50× the amount of methanol (in kg/h) than the methanol product recovery stream 178.

In some embodiments, the biomethanol production system 10 includes:

(a) a feed stream 106 containing, consisting essentially of, or consisting of biogas containing, consisting essentially of, or consisting of methane, water, and carbon dioxide;

(b) a reformer reactor 12 capable of reacting the biogas to form a syngas mixture containing, consisting essentially of, or consisting of hydrogen, carbon monoxide, and carbon dioxide;

(c) a methanol reactor 14 capable of reacting the syngas mixture to form a biomethanol product;

(d) a wash column 16 containing the syngas mixture and the biomethanol product, wherein the biomethanol product is capable of absorbing carbon dioxide from the syngas mixture; and (e) a flash column 18 comprising a vent capable of venting the absorbed carbon dioxide.

In some embodiments, the biomethanol production system 10 includes:

(a) a feed stream 106 containing, consisting essentially of, or consisting of biogas containing, consisting essentially of, or consisting of methane, water, and carbon dioxide;

(b) a reformer reactor 12 capable of reacting the biogas to form a syngas mixture containing, consisting essentially of, or consisting of hydrogen, carbon monoxide, and carbon dioxide;

(c) a first methanol reactor 14a capable of reacting the syngas mixture to form a biomethanol product;

(d) a second methanol reactor 14b capable of reacting the syngas mixture to form a biomethanol product;

(e) a wash column 16 containing the syngas mixture and the biomethanol product, wherein the biomethanol product is capable of absorbing carbon dioxide from the syngas mixture; and (f) a flash column 18 comprising a vent capable of venting the absorbed carbon dioxide.

The structure, arrangement, and elements of the biomethanol production system 10 described herein and depicted in FIG. 1 include alternative design choices and serve the purpose of adapting the biomethanol production system 10 to specific needs, such as specific input compositions or pressures, or specific output purity or yield, for example. This may give the system operators additional flexibility in configuring the system 10 to meet their needs related to, for example, the composition of the raw gas stream and/or the required purity of the biomethanol stream produced by the system.

The biomethanol production system 10 may comprise two or more embodiments disclosed herein.

Figure 2:
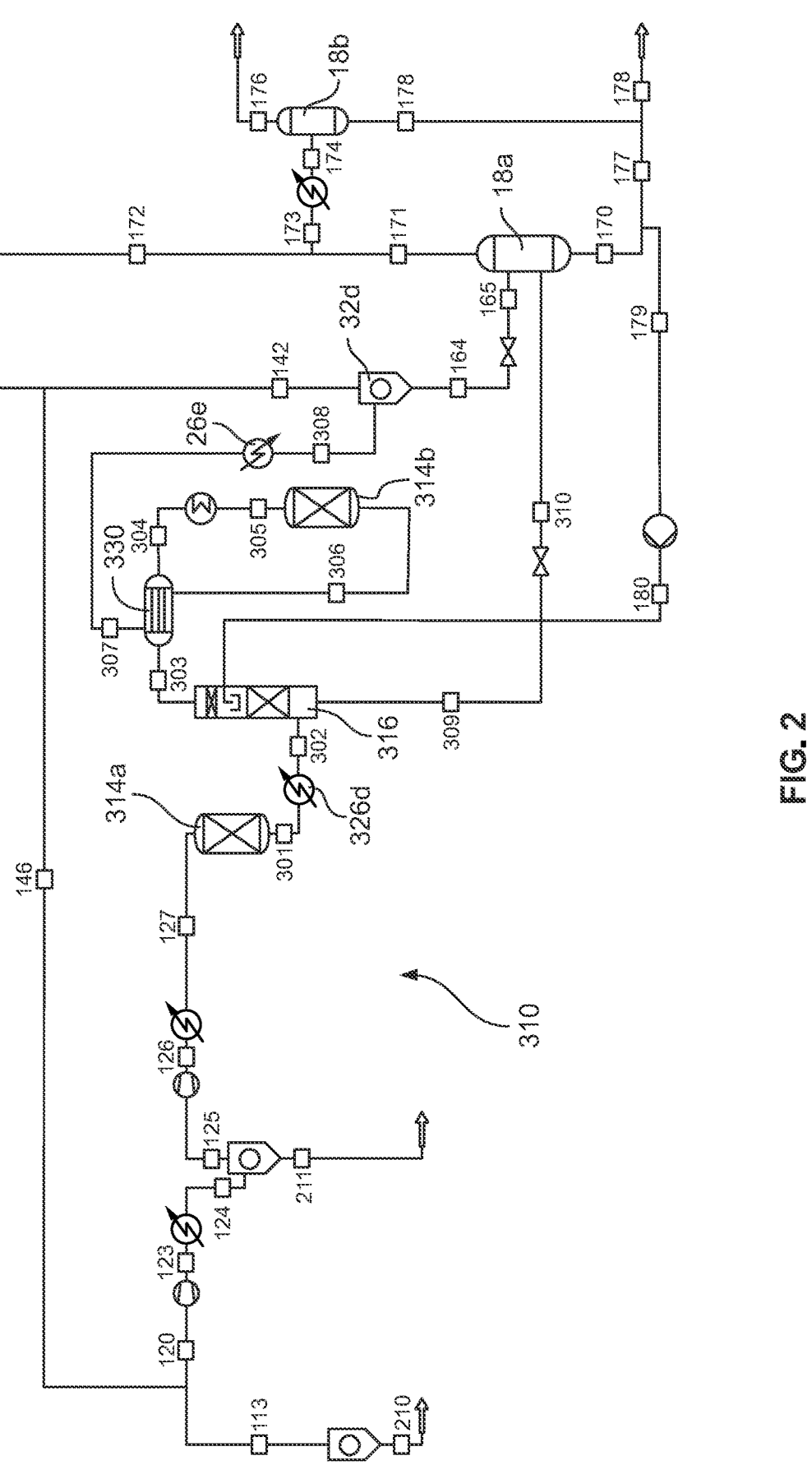
FIG. 2 schematically illustrates a biomethane production system according to another embodiment.

Referring now to FIG. 2, biomethanol production system 310 is shown. In an embodiment, the biomethanol production system 310 includes at least a reformer reactor (not shown), a methanol reactor 314a, 314b, a wash column 316, and a flash column 18a, 18b. In the biomethanol production system 310, the wash column is positioned between a first methanol reactor 314a and a second methanol reactor 314b. In the biomethanol production system 310, the system upstream of the first methanol reactor 314a may be any system disclosed herein.

The first methanol reactor 314a is in fluid communication with the reformer reactor and the wash column 316. The first methanol reactor 314a is upstream of the wash column 316, and downstream of the reformer reactor (not shown). The first methanol reactor 314a and the second methanol reactor 314b are in fluid communication with each other. The second gas stream 125 puts the first methanol reactor 314a in fluid communication with the reformer reactor. The first methanol reactor 314a has a feed side that is in fluid communication with the second gas stream 125. The product of the first methanol reactor 314a is discharged via the first methanol reactor discharge line 301. The first methanol reactor discharge line 301 contains more methanol than the second gas stream 125, based on total moles of methanol in the respective streams. In some embodiments, the first methanol reactor discharge line 301 contains at least 500%, or at least 1000%, or at least 1500%, or at least 2000%, or at least 2500% more methanol than the second gas stream 125, based on total moles of methanol in the respective streams. In another embodiment, the first methanol reactor discharge line 301 contains from 500% to 5000%, or from 1000% to 4000%, or from 2000% to 3000% more methanol than the second gas stream 125, based on total moles of methanol in the respective streams.

In an embodiment, the biomethanol production system 310 includes a fifth temperature control device 326d configured between the first methanol reactor 314a and the wash column 316. Suitable fifth temperature control devices 326d include devices that heat or cool the process stream, such as heat exchangers or electric heaters. In an embodiment, the fifth temperature control device 326d is configured to cool the process stream. In some embodiments, the fifth temperature control device 326d is configured to cool the process stream by at least 20° C., or at least 50° C., or at least 75° C., or at least 90° C. In another embodiment, the fifth temperature control device 326d is configured to cool the process stream by from 20° C. to 300° C., or from 50° C. to 300° C., or from 50° C. to 200° C., or from 50° C. to 100° C., or from 90° C. to 100° C. The biomethanol production system 310 includes a first continuing stream 302 that puts the fifth temperature control device 326d in fluid communication with the wash column 316.

The wash column 316 is in fluid communication with the first methanol reactor 314a, the second methanol reactor 314b, the reformer reactor, and the flash column 18. The first continuing stream 302 and a methanol recycle stream 180 are fed into the wash column 316. The first continuing stream 302 puts the wash column 316 in fluid communication with the fifth temperature control device 326d. The methanol recycle stream 180 puts the wash column 316 in fluid communication with the flash column 18.

In an embodiment, the wash column 316 contains, consists essentially of, or consists of the contents of the first continuing stream 302 and the methanol recycle stream 180. In some embodiments, the first continuing stream 302 contains, consists essentially of, or consists of (i) methane, (ii) carbon dioxide, (iii) water, (iv) carbon monoxide, (v) hydrogen, (vi) methanol, and (vii) nitrogen. In another embodiment, the first continuing stream 302 contains, consists essentially of, or consists of, based on the total mole percentage of the first continuing stream 302, (i) from 0.1 mol %, or 0.2 mol %, or 0.3 mol %, or 0.4 mol % to 0.5 mol %, or 0.6 mol %, or 0.8 mol %, or 1.0 mol %, or 5.0 mol % methane; (ii) from 1 mol %, or 2 mol %, or 3 mol %, or 4 mol %, or 5 mol % to 6 mol %, or 8 mol %, or 10 mol %, or 15 mol % carbon dioxide; (iii) from 0 mol %, or greater than 0 mol %, or 0.01 mol % to 0.02 mol %, or 0.05 mol % water; (iv) from 10 mol %, or 15 mol %, or 20 mol %, or 25 mol %, or 30 mol % to 35 mol %, or 40 mol %, or 45 mol %, or 50 mol % carbon monoxide, (v) from 40 mol %, or 45 mol %, or 50 mol %, or 55 mol %, or 60 mol % to 65 mol %, or 70 mol %, or 75 mol % hydrogen; (vi) from 0 mol %, or greater than 0 mol %, or 0.01 mol %, or 0.05 mol %, or 0.07 mol % to 0.10 mol %, or 0.50 mol %, or 1.0 mol % methanol; and (vii) from greater than 0 mol %, or 0.5 mol %, or 1.0 mol %, or 1.5 mol % to 2.0 mol %, or 5.0 mol %, or 10 mol % nitrogen. In a further embodiment, the first continuing stream 302 contains, consists essentially of, or consists of, based on the total mole percentage of the first continuing stream 302, (i) from 0.1 mol % to 5.0 mol %, or from 0.1 mol % to 1 mol %, or from 0.2 mol % to 0.8 mol %, or from 0.4 mol % to 0.5 mol % methane; (ii) from 1 mol % to 15 mol %, or from 1 mol % to 10 mol %, or from 3 mol % to 8 mol %, or from 5 mol % to 6 mol % carbon dioxide; (iii) from 0 mol % to 0.05 mol %, or from greater than 0 mol % to 0.05 mol %, or from 0.01 mol % to 0.05 mol %, or from 0.01 mol % to 0.02 mol % water; (iv) from 10 mol % to 50 mol %, or from 15 mol % to 50 mol %, or from 25 mol % to 40 mol %, or from 30 mol % to 35 mol % carbon monoxide; (v) from 40 mol % to 75 mol %, or from 40 mol % to 70 mol %, or from 50 mol % to 75 mol %, or from 60 mol % to 65 mol % hydrogen; (vi) from 0 mol % to 1.0 mol %, or from greater than 0 mol % to 1.0 mol %, or from 0.01 mol % to 1.0 mol %, or from 0.05 mol % to 0.50 mol %, or from 0.07 mol % to 0.10 mol % methanol; and (vii) from greater than 0 mol % to 10 mol %, or from 0.5 mol % to 10 mol %, or from 1.0 mol % to 5.0 mol %, or from 1.5 mol % to 2.0 mol % nitrogen. In some embodiments, the methanol recycle stream 180 contains, consists essentially of, or consists of (i) methane, (ii) carbon dioxide, (iii) water, (iv) carbon monoxide, (v) hydrogen, (vi) methanol, and (vii) nitrogen. In another embodiment, the methanol recycle stream 180 contains, consists essentially of, or consists of, based on the total mole percentage of the methanol recycle stream 180, (i) from 0 mol %, or greater than 0 mol %, or 0.00001 mol % to 0.00005 mol %, or 0.00010 mol % methane; (ii) from 0 mol %, or greater than 0 mol %, or 0.01 mol % to 0.05 mol %, or 0.10 mol % carbon dioxide; (iii) from 0 mol %, or greater than 0 mol %, or 0.01 mol %, or 0.10 mol % to 0.20 mol %, or 0.50 mol %, or 1.0 mol % water; (iv) from 0 mol %, or greater than 0 mol %, or 0.0001 mol % to 0.0005 mol %, or 0.0010 mol % carbon monoxide; (v) from 0 mol %, or greater than 0 mol %, or 0.0001 mol % to 0.0005 mol %, or 0.0010 mol % hydrogen; (vi) from 90 mol %, or 95 mol %, or 98 mol %, or 99 mol % to 99.8 mol %, or 99.9 mol %, or less than 100 mol %, or 100 mol % methanol; and (vii) from 0 mol %, or greater than 0 mol %, or 0.00001 mol % to 0.00005 mol %, or 0.00010 mol %, or 0.00050 mol % nitrogen. In some embodiments, the methanol recycle stream 180 contains, consists essentially of, or consists of, based on the total mole percentage of the methanol recycle stream 180, (i) from 0 mol % to 0.00010 mol %, or from greater than 0 mol % to 0.00010 mol %, or from 0.00001 mol % to 0.00005 mol % methane; (ii) from 0 mol % to 0.10 mol %, or from greater than 0 mol % to 0.10 mol %, or from 0.01 mol % to 0.10 mol %, or from 0.01 mol % to 0.05 mol % carbon dioxide; (iii) from 0 mol % to 1.0 mol %, or from greater than 0 mol % to 1.0 mol %, or from 0.01 mol % to 1.0 mol %, or from 0.10 mol % to 0.50 mol %, or from 0.01 mol % to 0.20 mol % water; (iv) from 0 mol % to 0.0010 mol %, or from greater than 0 mol % to 0.0010 mol %, or from 0.0001 mol % to 0.0010 mol %, or from 0.0001 mol % to 0.0005 mol % carbon monoxide; (v) from 0 mol % to 0.0010 mol %, or from greater than 0 mol % to 0.0010 mol %, or from 0.0001 mol % to 0.0010 mol %, or from 0.0001 mol % to 0.0005 mol % hydrogen; (vi) from 90 mol % to 100 mol %, or from 90 mol % to less than 100 mol %, or from 90 mol % to 99.9 mol %, or from 95 mol % to 99.9 mol %, or from 98 mol % to 99.9 mol %, or from 99.0 mol % to 99.9 mol % methanol; and (vii) from 0 mol % to 0.00050 mol %, or from greater than 0 mol % to 0.00050 mol %, or from 0.00001 mol % to 0.00050 mol %, or from 0.00001 mol % to 0.00005 mol % nitrogen.

Not wishing to be bound by any particular theory, it is believed that the methanol from the methanol recycle stream 180 absorbs carbon dioxide from the first continuing stream 302 in the wash column 316. This is advantageous because excess carbon dioxide is removed from the process stream without requiring the addition of a separate component feed (e.g., hydrogen or a solvent such as water), or a membrane to remove the carbon dioxide. Rather, the present biomethanol production system 310 is configured to remove excess carbon dioxide from the process stream using at least some of the methanol product produced by the biomethanol production system 310. This may increase the efficiency of the system 310, thereby presenting an opportunity for significant cost savings for the system operator.

The wash column 316 discharges the process stream via a wash process stream discharge line 303. The methanol containing the absorbed carbon dioxide is discharged from the wash column 316 via a $CO_2$-methanol line 309. The wash process stream discharge line 303 puts the wash column 316 in fluid communication with the second methanol reactor 314*b*. The $CO_2$-methanol line 309 puts the wash column 316 in fluid communication with the first flash column 18*a*. The wash process stream discharge line 303 contains less carbon dioxide than the first continuing stream 302. In other words, the process stream contains less carbon dioxide when it is discharged from the wash column 316 relative to the carbon dioxide content of the process stream before it enters the wash column 316. In some embodiments, the wash process stream discharge line 303 contains at least 50% less, or at least 75% less, or at least 80% less, or at least 90% less, or at least 95% less carbon dioxide than the first continuing stream 302, based on the total moles of carbon dioxide contained in the respective stream. In another embodiment, the wash process stream discharge line 303 contains from 50% to 100%, or from 50% to less than 100%, or from 75% to 99.9%, or from 80% to 99.9%, or from 90% to 99.9%, or from 95% to 99.9% less carbon dioxide than the first continuing stream 302, based on the total moles of carbon dioxide contained in the respective stream. In some embodiments, the ratio of moles of carbon dioxide in the first continuing stream 302 to the moles of carbon dioxide in the wash process stream discharge line 303 is from 80:1, or 75:1, or 70:1, or 60:1, or 55:1 to 50:1, or 45:1, or 40:1, or 35:1. In another embodiment, the ratio of moles of carbon dioxide in the first continuing stream 302 to the moles of carbon dioxide in the wash process stream discharge line 303 is from 80:1 to 35:1, or from 80:1 to 45:1, or from 70:1 to 45:1, or from 60:1 to 45:1, or from 55:1 to 50:1.

The $CO_2$-methanol line 309 contains more carbon dioxide than the methanol recycle stream 180. In other words, the methanol stream contains more carbon dioxide when it is discharged from the wash column 316 relative to the carbon dioxide content of the methanol stream before it enters the wash column 316. In some embodiments, the $CO_2$-methanol line 309 contains at least 100%, or at least 500%, or at least 1000%, or at least 1500%, or at least 2000% more carbon dioxide than the methanol recycle stream 180, based on the total moles of carbon dioxide contained in the respective stream. In another embodiment, the $CO_2$-methanol line 309 contains from 100% to 5000%, or from 500% to 4000%, or from 1000% to 3000%, or from 2000% to 2500% more carbon dioxide than the methanol recycle stream 180, based on the total moles of carbon dioxide contained in the respective stream. In some embodiments, the ratio of moles of carbon dioxide in the $CO_2$-methanol line 309 to the moles of carbon dioxide in the methanol recycle stream 180 is from 10:1, or 15:1, or 20:1 to 25:1, or 30:1, or 35:1, or 40:1, or 50:1. In another embodiment, the ratio of moles of carbon dioxide in the $CO_2$-methanol line 309 to the moles of carbon dioxide in the methanol recycle stream 180 is from 10:1 to 50:1, or from 15:1 to 40:1, or from 20:1 to 30:1, or from 20:1 to 25:1.

In some embodiments, the biomethanol production system 310 includes a heat exchanger 330 in fluid communication with the wash column 316 and the second methanol reactor 314a. In an embodiment, the heat exchanger 330 places the wash process stream discharge line 303 in fluid communication with the second methanol reactor 314b. The heat exchanger 330 has a first exchange discharge line 304 that is in fluid communication with the wash process stream discharge line 303 and the wash column 316. In some embodiments, the temperature of the first exchange discharge line 304 is higher than the temperature of the wash process stream discharge line 303. In an embodiment, the temperature of the first exchange discharge line 304 is at least 100° C., or at least 125° C., or at least 150° C., or at least 160° C. greater than the temperature of the wash process stream discharge line 303. In another embodiment, the temperature of the first exchange discharge line 304 is from 100° C. to 500° C., or from 100° C. to 300° C., or from 100° C. to 200° C., or from 150° C. to 200° C. greater than the temperature of the wash process stream discharge line 303. The heat exchanger 330 has a second exchange discharge line 307 that is in fluid communication with a second methanol reactor discharge line 306. In some embodiments, the temperature of the second exchange discharge line 307 is lower than the temperature of the second methanol reactor discharge line 306. In an embodiment, the temperature of the second exchange discharge line 307 is at least 50° C., or at least 75° C., or at least 100° C. lower than the temperature of the second methanol reactor discharge line 306. In another embodiment, the temperature of the second exchange discharge line 307 is from 50° C. to 500° C., or from 50° C. to 300° C., or from 50° C. to 200° C., or from 100° C. to 200° C., or from 100° C. to 150° C. lower than the temperature of the second methanol reactor discharge line 306. The heat exchanger 330 facilitates the use of the temperature difference between the wash process stream discharge line 303 and the second methanol reactor discharge line 306 to cool the second methanol reactor discharge line 306 contents and heat the wash process stream discharge line 303 contents. In other words, thermal energy of the second methanol reactor discharge line 306 is transferred to the wash process stream discharge line 307. A second continuing stream 304 and a third continuing stream 305 place the heat exchanger 330 in fluid communication with the second methanol reactor 314b.

In some embodiments, the biomethanol production system 310 includes a second methanol reactor 314b. The second methanol reactor 314b is in fluid communication with the heat exchanger 330 and a fifth separator 32d. The first exchange discharge line 304 and the second methanol reactor discharge line 306 put the second methanol reactor 314b in fluid communication with the fifth separator 32d. The second methanol reactor 314b has a feed side that is in fluid communication with the first exchange discharge line 304. The product of the second methanol reactor 314b is discharged via the second methanol reactor discharge line 306. The second methanol reactor discharge line 306 contains more methanol than the first exchange discharge line 304, based on total moles of methanol in the respective streams. In some embodiments, the second methanol reactor discharge line 306 contains at least 500%, or at least 1000%, or at least 1500%, or at least 2000%, or at least 4000%, or at least 6000%, or at least 7000% more methanol than the first exchange discharge line 304, based on total moles of methanol in the respective streams. In another embodiment, the second methanol reactor discharge line 306 contains from 500% to 10000%, or from 5000% to 10000%, or from 7000% to 8000% more methanol than the first exchange discharge line 304, based on total moles of methanol in the respective streams.

In some embodiments, the biomethanol production system 10 includes a sixth temperature control device 26e configured between the heat exchanger 330 and the fifth separator 32d. Suitable sixth temperature control devices 26e include devices that heat or cool the process stream, such as heat exchangers or electric heaters. In an embodiment, the sixth temperature control device 26e is configured to cool the process stream. In some embodiments, the sixth temperature control device 26e is configured to cool the process stream by at least 40° C., or at least 50° C., or at least 75° C., or at least 80° C. In another embodiment, the sixth temperature control device 26e is configured to cool the process stream by from 40° C. to 200° C., or from 50° C. to 150° C., or from 50° C. to 100° C., or from 75° C. to 100° C., or from 80° C. to 90° C.

In some embodiments, the biomethanol production system 10 includes a fifth separator 32d in fluid communication with the sixth temperature control device 26e, the first flash column 18a, and the second flash column 18b.

Figure 3:
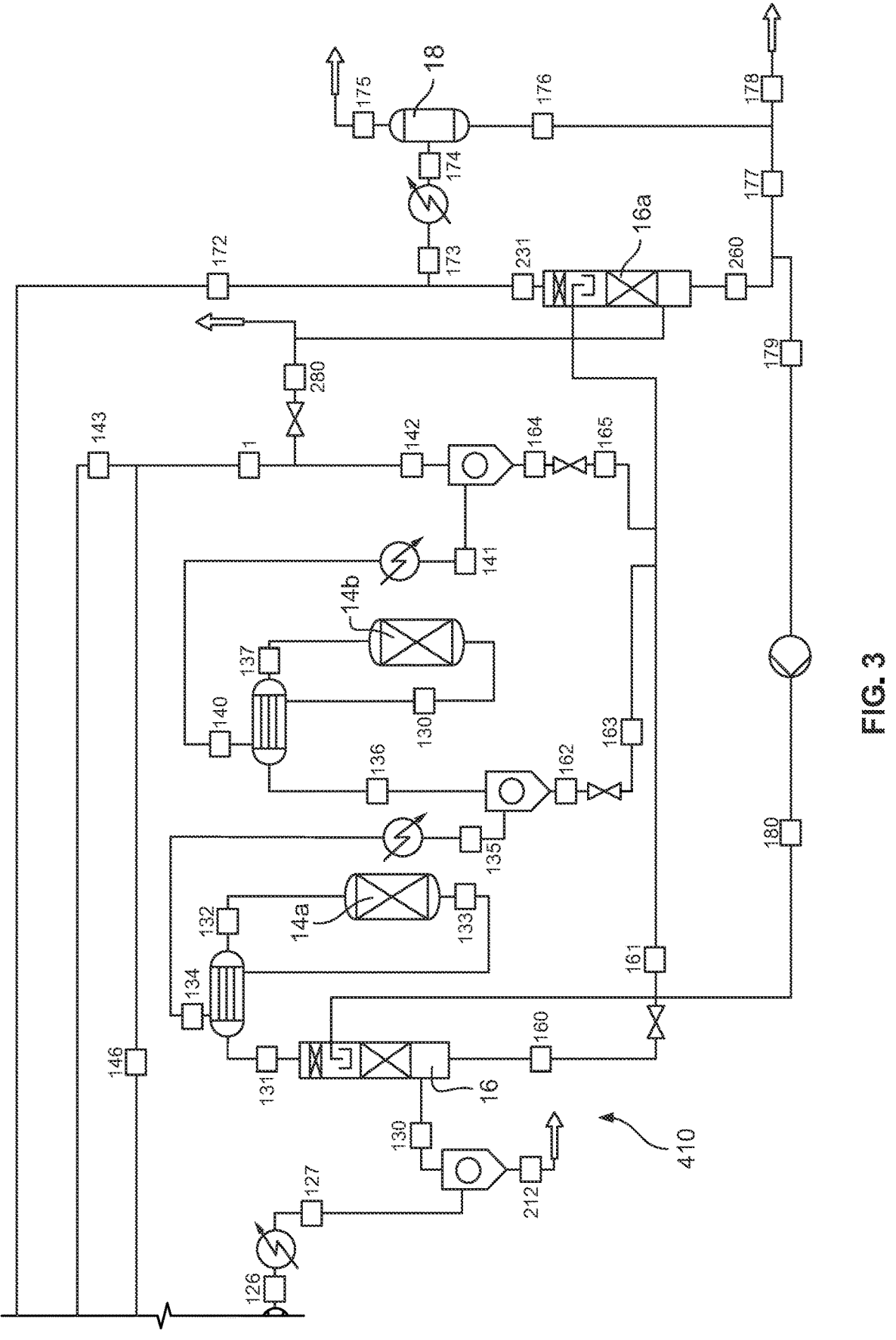
FIG. 3 schematically illustrates a biomethane production system according to another embodiment.
Figure 5:
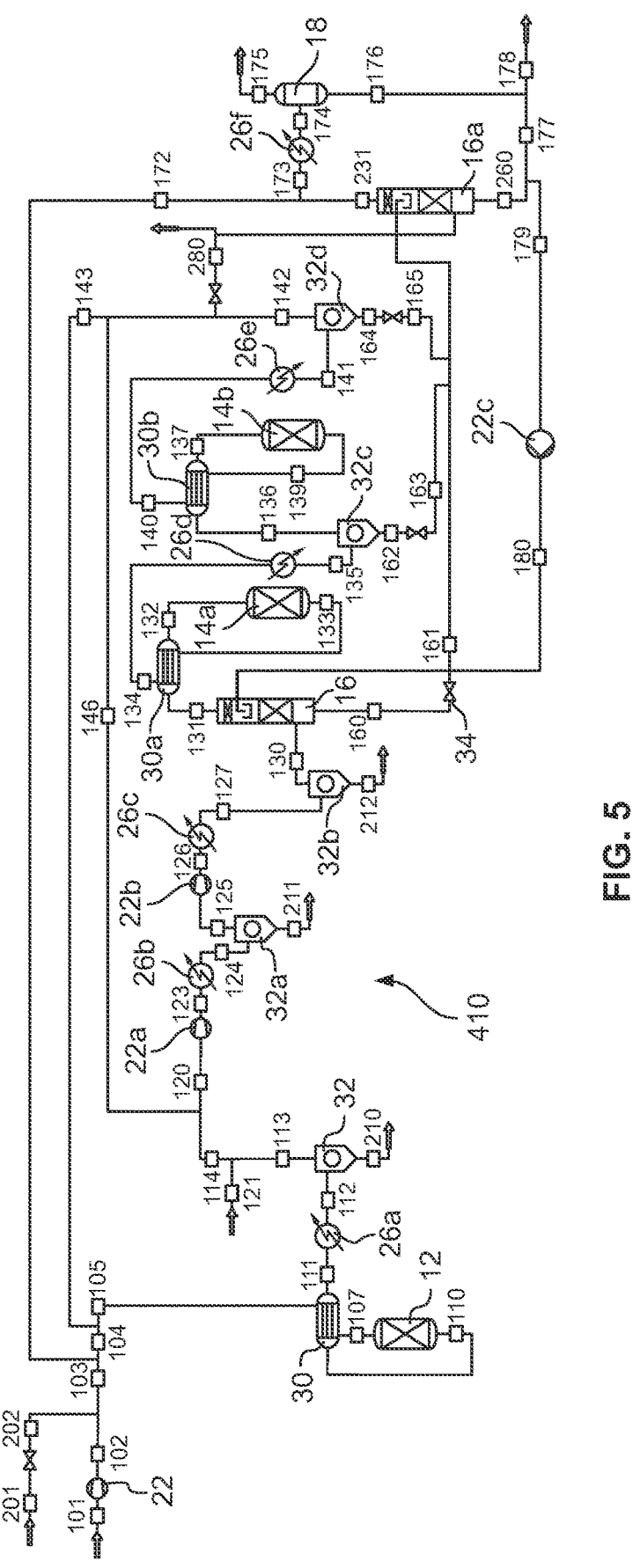
FIG. 5 schematically illustrates a biomethane production system according to another embodiment.

Referring now to FIGS. 3 and 5, a biomethanol production system 410 is shown. In an embodiment, the biomethanol production system 410 includes at least a reformer reactor (not shown), a methanol reactor 14a, 14b, a first wash column 16, a second wash column 16a, and a flash column 18. In the biomethanol production system 410, the second wash column 16a is positioned downstream of the methanol reactors 14a, 14b. In the biomethanol production system 410, the system upstream of the first wash column 16, the first methanol reactor 14a, the second methanol reactor 14b, the fourth separator 32c, and the fifth separator 32d may be any system disclosed herein.

The structure, arrangement, and elements of the biomethanol production system 410 described herein and depicted in FIGS. 3 and 5 include alternative design choices and serve the purpose of adapting the biomethanol production system 10 to specific operational parameters, such as specific input compositions or pressures, or specific output purity or yield. The alternative design choices may give the operators additional flexibility in configuring the system 410 to meet their needs related to, for example, the composition of the raw gas stream and/or the required purity of the biomethanol stream produced by the system.

The second wash column 16a is configured to reduce the partial pressure of the carbon dioxide and separate surplus nitrogen from the biomethanol production system 410. In an embodiment, the second wash column 16a has a feed side that is in fluid communication with the $CO_2$-methanol line 160. The nitrogen-containing gas stream is discharged from the second wash column 16a via a nitrogen discharge line 280. The methanol containing the absorbed carbon dioxide is discharged from the second wash column 16b via the second $CO_2$-methanol line 231. The methanol product is discharged from the second wash column 16a via the wash discharge line 260. The nitrogen in the nitrogen discharge line 280 may be collected, recycled and/or discarded. The second $CO_2$-methanol line 231 is in fluid communication with the flash column 18. The wash discharge line 260 is in fluid communication with the first wash column 16 and the methanol product recovery stream 178. The $CO_2$-methanol line 160 is transferred to the second wash column 16a to flash off the carbon dioxide in the gas phase. Not wishing to be bound by any particular theory, it is believed the flashing is more effective when the nitrogen discharge line 280 (i.e., purge stream) from the methanol loop is added to the bottom of the second wash column 16a. This reduces the partial pressure of the carbon dioxide in the gas phase (because the purge stream contains almost no carbon dioxide). Consequently, carbon dioxide can be flashed from the liquid methanol before it is pumped to the wash column 16 to capture carbon dioxide. This process may increase the efficiency of the system 410, providing cost savings for system operators.

In some embodiments, the biomethanol production system 10, 310, 410 is void of amines. In other words, the biomethanol production system 10, 310, 410 excludes amines. Not wishing to be bound by any particular theory, it is believed that amine treatment would require a physically large system in order to be economically efficient. Therefore, amine treatment is inefficient for small biomethanol production systems that may be used by biogas producers on-site.

In some embodiments, the biomethanol production system 10, 310, 410 is void of a fresh hydrogen feed downstream of the reformer reactor 12. In other words, no hydrogen is added into the process stream downstream of the reformer reactor 12.

In some embodiments, the biomethanol production system 10, 310, 410 is equipped with a hydrogen feed line downstream of the reformer reactor 12 that is coupled to at least one valve. The at least one valve may be opened and closed such that the operator may adapt the carbon dioxide removal capabilities of the biomethanol production system 10, 310, 410 as appropriate. As a non-limiting example, the operator could close the at least one valve when no additional carbon dioxide removal is needed beyond what can be provided by the other components of the system 10, 310, 410. As an additional non-limiting example, the operator could open the at least one valve (fully or partially) when the operator desires to further remove carbon dioxide from the biomethanol production system 10, 310, 410.

In alternate embodiments (not shown), the biomethanol production system 10, 310, 410 is equipped with a hydrogen feed line downstream of the reformer reactor 12. By equipping the biomethanol production system 10, 310, 410 with a hydrogen feed line downstream of the reformer reactor 12, the system enables a user to remove the excess carbon dioxide via two modes or methods, including (a) the wash column 16, methanol reactor 14, and flash tank 18 loop disclosed herein, and (b) hydrogen addition downstream of the reformer reactor. Including the two modes or methods may be advantageous if the operator, for example, wishes to use mode (b) as a backup for mode (a). This may allow for the biomethanol production system 10, 310, and 410 to provide the advantages described herein while also increasing the resiliency of the system 10, 310, and 410 via redundancy.

In some embodiments, the biomethanol production system 10, 310, 410 is void of a membrane configured to isolate carbon dioxide from the remaining contents of the process stream. Not wishing to be bound by any particular theory, it is believed that the use of membranes configured to isolate carbon dioxide from the remaining contents of the process stream would require pressurization of the biogas upstream of the membrane, and depressurization of the biogas after passing through the membrane to reach optimum operating conditions for the reformer reactor. The additional pressurization and depressurization devices required for membrane use may increase the costs of the system.

In some embodiment, the biomethanol production system 10, 310, 410 is void of a pressure swing absorption unit. In other words, the biomethanol production system 10, 310, 410 excludes pressure swing absorption technology. In alternate embodiments (not shown), the biomethanol production system 10, 310, 410 includes a pressure swing absorption unit to remove targeted compounds from the process stream (s).

In some embodiments, the biomethanol production system 10, 310, 410 comprises (a) a feed stream; (b) a reformer reactor configured to react the feed stream to create a syngas mixture; (c) a methanol reactor configured to react the syngas mixture to form a biomethanol product; and (d) a wash column configured to absorb carbon dioxide from the syngas mixture.

In some embodiments, the biomethanol production system 10, 310, 410 may further comprise (e) a device configured to release the absorbed carbon dioxide from the biomethanol stream and vent the absorbed carbon dioxide from the biomethanol production system. Optionally, the device in step (e) may be provided as a flash column comprising a vent capable of venting the absorbed carbon dioxide.

In some embodiments, the biomethanol system 10, 310, 410 further comprises (f) a methanol recycle stream that puts the device in fluid communication with the wash column, the methanol recycle stream comprising biomethanol discharged from the device of step (e); and (g) a $CO_2$-methanol line that puts the wash column in fluid communication with the device, the $CO_2$-methanol line comprising the carbon dioxide absorbed in the biomethanol product discharged from the wash column. In addition, the biomethanol system may further comprise (h) a wash process stream discharge line that puts the wash column in fluid communication with the methanol reactor, the wash process stream discharge line comprising syngas mixture discharged from the wash column.

Advantageously, in the above-described embodiments, carbon dioxide is removed from the system without requiring the addition of a separate component feed (e.g., hydrogen or a solvent such as water), or a membrane to remove the carbon dioxide, or pressure swing absorption. Rather, the biomethanol production system may remove carbon dioxide from the process by using at least a portion of the methanol product produced by the biomethanol production system. Removal of carbon dioxide in this manner may increase the efficiency of the system, thereby presenting an opportunity for significant cost savings for the system operator.

Method

A method for removing carbon dioxide from a biomethanol production system is provided. The method includes (a) reacting biogas in a reformer reactor to form a syngas mixture comprising hydrogen, carbon monoxide, and carbon dioxide; (b) feeding the syngas mixture to a wash column and forming a process stream; (c) feeding the process stream to a first methanol reactor and reacting process stream to form biomethanol; (d) feeding the biomethanol from the methanol reactor to a flash column and then to the wash column; (e) absorbing carbon dioxide from the syngas mixture in the wash column with the biomethanol to form a $CO_2$-methanol stream; and (f) recycling the $CO_2$-methanol stream by feeding it to the flash column and releasing the absorbed carbon dioxide.

In some embodiments of the above-described method, the carbon dioxide released in step (f) is vented from the flash column. In some embodiments of the above-described method, a second methanol reactor is positioned between the first methanol reactor and the flash column. In some embodiments, the above-described method excludes at least one of: (i) treating the syngas mixture, the biomethanol, and the $CO_2$-methanol stream with amines; and (ii) treating the syngas mixture, the biomethanol, and the $CO_2$-methanol stream with a membrane configured to isolate carbon dioxide from components of the syngas mixture, the biomethanol, and the $CO_2$-methanol stream.

Advantageously, in the above-described method, carbon dioxide is removed without requiring the addition of a separate component feed (e.g., hydrogen or a solvent such as water), or a membrane to remove the carbon dioxide, or pressure swing absorption. Rather, the biomethanol production system may remove carbon dioxide from the process by using at least a portion of the methanol product produced by the biomethanol production system. Removal of carbon dioxide in this manner may increase the efficiency of the system, thereby presenting an opportunity for significant cost savings for the system operator.

The biomethanol production system may be any biomethanol production system 10, 310, 410 disclosed herein.

Figure 4:
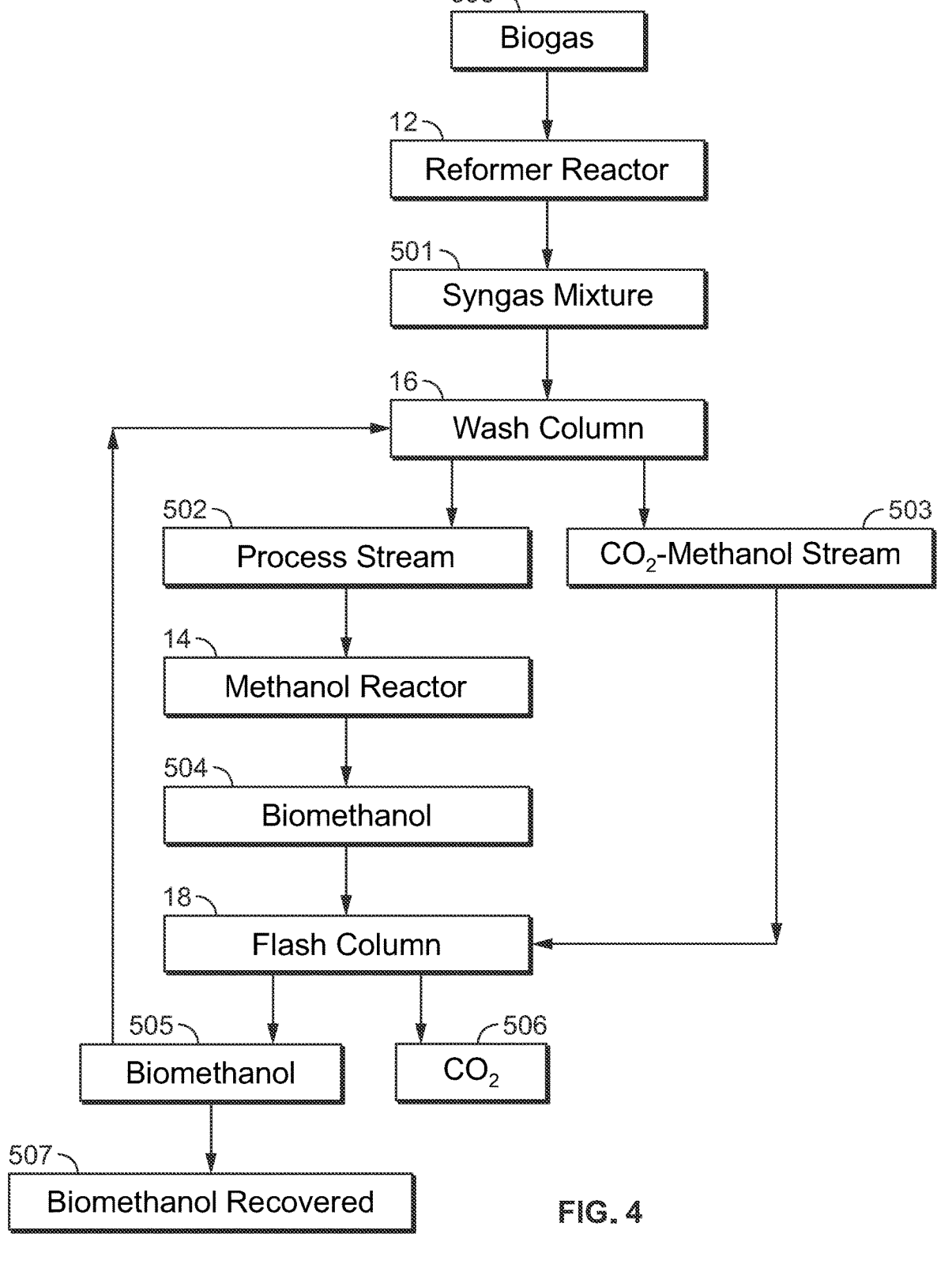
FIG. 4 schematically illustrates a method for removing carbon dioxide from a biomethanol production system according to one embodiment.

The method for removing carbon dioxide from a biomethanol production system is illustrated schematically in FIG. 4. In some embodiments, the method for removing carbon dioxide from a biomethanol production system includes:

(a) providing a biogas 500 comprising methane, water, and carbon dioxide;

(b) reacting the biogas 500 in a reformer reactor 12 to form a syngas mixture 501 comprising hydrogen, carbon monoxide, and carbon dioxide;

(c) feeding the syngas mixture 501 to a wash column 16 and forming a process stream 502, wherein the process stream 502 contains less carbon dioxide than the syngas mixture 501;

(d) feeding the process stream 502 to a methanol reactor 14 and reacting the contents of the process stream 502 to form biomethanol 504;

(e) feeding the biomethanol 504 from the methanol reactor 14 to a flash column 18;

(f) feeding the biomethanol 505 from the flash column 18 to the wash column 16;

(g) absorbing carbon dioxide from the syngas mixture 501 in the wash column 16 with the biomethanol 505 from the flash column 18 to form a $CO_2$-methanol stream 503, wherein the $CO_2$-methanol stream 503 contains more carbon dioxide than the biomethanol 505 from the flash column 18;

(h) feeding the $CO_2$-methanol stream 503 to the flash column 18 and releasing the absorbed carbon dioxide 506 from the biomethanol 505;

(i) venting the carbon dioxide 506 from the flash column 18; and (j) recovering the biomethanol 507.

In some embodiments, the method includes feeding the syngas mixture to a wash column and forming a process stream, wherein the process stream contains less carbon dioxide than the syngas mixture. In other words, the process stream contains less carbon dioxide when it is discharged from the wash column 16 relative to the carbon dioxide content of the syngas mixture before it enters the wash column 16. In some embodiments, the process stream contains at least 50% less, or at least 75% less, or at least 80% less, or at least 90% less, or at least 95% less carbon dioxide than the syngas mixture, based on the total moles of carbon dioxide contained in the respective stream. In another embodiment, the process stream contains from 50% to 100%, or from 50% to less than 100%, or from 75% to 99.9%, or from 80% to 99.9%, or from 90% to 99.9%, or from 95% to 99.9% less carbon dioxide than the syngas mixture, based on the total moles of carbon dioxide contained in the respective stream. In some embodiments, the ratio of moles of carbon dioxide in the syngas mixture to the moles of carbon dioxide in the process stream is from 80:1, or 75:1, or 70:1, or 60:1, or 55:1 to 50:1, or 45:1, or 40:1, or 35:1. In another embodiment, the ratio of moles of carbon dioxide in the syngas mixture to the moles of carbon dioxide in the process stream is from 80:1 to 35:1, or from 80:1 to 45:1, or from 70:1 to 45:1, or from 60:1 to 45:1, or from 55:1 to 50:1.

In some embodiments, the method includes absorbing carbon dioxide from the syngas mixture in the wash column with the biomethanol from the flash column to form a $CO_2$-methanol stream, wherein the $CO_2$-methanol stream contains more carbon dioxide than the biomethanol from the flash column.

The $CO_2$-methanol stream contains more carbon dioxide than the biomethanol stream from the flash column. In other words, the $CO_2$-methanol stream contains more carbon dioxide when it is discharged from the wash column 16 relative to the carbon dioxide content of the biomethanol stream from the flash column, before it enters the wash column 16. In some embodiments, the $CO_2$-methanol stream contains at least 100%, or at least 500%, or at least 1000%, or at least 1500%, or at least 2000% more carbon dioxide than the biomethanol stream from the flash column, based on the total moles of carbon dioxide contained in the respective stream. In another embodiment, the $CO_2$-methanol stream contains from 100% to 5000%, or from 500% to 4000%, or from 1000% to 3000%, or from 2000% to 2500% more carbon dioxide than the biomethanol stream from the flash column, based on the total moles of carbon dioxide contained in the respective stream. In some embodiments, the ratio of moles of carbon dioxide in the $CO_2$-methanol stream to the moles of carbon dioxide in the biomethanol stream from the flash column is from 10:1, or 15:1, or 20:1 to 25:1, or 30:1, or 35:1, or 40:1, or 50:1. In another embodiment, the ratio of moles of carbon dioxide in the $CO_2$-methanol stream to the moles of carbon dioxide in the biomethanol stream from the flash column is from 10:1 to 50:1, or from 15:1 to 40:1, or from 20:1 to 30:1, or from 20:1 to 25:1.

In some embodiments, the method includes recycling at least twice the amount of methanol that is recovered. In other words, the methanol recycle stream 180 contains at least two times, or at least three times, or at least ten times, or at least twenty times, or at least thirty times, or at least forty times, or at least forty-five times the amount of methanol (in kg/h) than the methanol product recovery stream 178. In some embodiments, the methanol recycle stream 180 contains from two times (2×), or three times (3×), or ten times (10×), or twenty times (20×), or thirty times (30×), or forty times (40×), or forty-five times (45×) to fifty times (50×), or seventy-five times (75×), or one hundred times (100×) the amount of methanol (in kg/h) than the methanol product recovery stream 178. In another embodiment, the methanol recycle stream 180 contains from 2× to 100×, or from 10× to 100×, or from 20× to 100×, or from 30× to 100×, or from 40× to 100×, or from 45× to 100×, or from 40× to 75×, or from 40× to 50×, or from 45× to 50× the amount of methanol (in kg/h) than the methanol product recovery stream 178.

In some embodiments, no hydrogen is added into the syngas mixture, the process stream, the biomethanol stream, or the CO₂-methanol stream downstream of the reformer reactor.

In some embodiments, the system includes a hydrogen feed line that is coupled to at least one valve. The at least one valve may be opened and closed such that the operator may adapt the carbon dioxide removal capabilities of the system as appropriate. As a non-limiting example, the operator could close the at least one valve when no additional carbon dioxide removal is needed beyond what can be provided by the other components of the system. As an additional non-limiting example, the operator could open the at least one valve (fully or partially) when the operator desires to further remove carbon dioxide from the system. The hydrogen from said hydrogen feed line may be added into the syngas mixture, the process stream, the biomethanol stream, or the CO₂-methanol stream downstream of the reformer reactor as deemed appropriate by the operator.

In some embodiments, the method excludes the use of amines. In other words, the biomethanol production system 10, 310, 410 is void of amines.

In some embodiments, the method excludes the use of a membrane configured to isolate carbon dioxide from the remaining contents of the syngas mixture, the process stream, the biomethanol stream, or the CO₂-methanol stream. In other words, the biomethanol production system 10, 310, 410 is void of a membrane configured to isolate carbon dioxide from the remaining contents of the syngas mixture, the process stream, the biomethanol stream, or the CO₂-methanol stream. This may increase the cost savings provided by the system 10, 310, 410.

EXAMPLES

Example 1

Example 1 is a biomethanol production system 10 configured as shown in FIG. 1. The parameters and content of the various streams is provided below in Table 1. In Example 1, the lines 126, 127, 145 are continuing lines. The carbon dioxide recycle line 172 has no flow in Example 1. However, it is understood that the carbon dioxide recycle line 172 may be used to take unreacted methane back to the reformer reactor 12. The second vent stream 175 is a purge line that may be vented through a flare. The first liquid stream 210, the second liquid stream 211, and the third liquid stream 212 contain surplus water from the system, and the contents of the liquid streams 210, 211, 212 are discarded. The hydrogen feed line 121 has no flow in Example 1.

The reformer reactor 12 of Example 1 is operated at a temperature of 850° C. (1123.15° K), has a heat duty of 18.0390 kW, and an overall heat of reaction of 16.2498 kW. The methanol reactor 14a of Example 1 is operated at a temperature of 225° C. (498.15° K) and has a heat duty of −6.3172 kW. The methanol reactor 14b of Example 1 is operated at a temperature of 225° C. (498.15° K) and has a heat duty of −3.1450 kW.

TABLE 1

| Stream # | | 101 | 102 | 103 | 104 | 105 | 106 | 107 | 110 |
|---|---|---|---|---|---|---|---|---|---|
| Stream Name | | inlet gas line | feed gas line | first continuing line | second continuing line | third continuing line | feed stream | first exchange discharge line | reformer discharge line |
| Molar Flow (kmol/h) | | 0.4569 | 0.4569 | 0.7899 | 0.7899 | 0.7899 | 0.7899 | 0.7899 | 1.3190 |
| Mass Flow (kmol/h) | | 12.3440 | 12.3440 | 18.3440 | 18.3440 | 18.3440 | 18.3440 | 18.3440 | 18.3438 |
| Temp. (° C.) | | 20.0000 | 57.2180 | 90.9529 | 90.9529 | 90.9529 | 90.9529 | 810.000 | 850.0000 |
| Pressure (bar) | | 1.0000 | 1.5000 | 1.5000 | 1.5000 | 1.5000 | 1.5000 | 1.5000 | 1.5000 |
| Vapor Mole Fraction | | 1.000 | 1.000 | 0.9908 | 0.9908 | 0.9908 | 0.9908 | 1.000 | 1.000 |
| Enth (kW) | | −25.692 | −25.519 | −47.636 | −47.636 | −47.636 | −47.636 | −40.052 | −22.013 |
| Actual Volume (m³/h) | | 11.1006 | 8.3407 | 15.7010 | 15.7010 | 15.7010 | 15.7010 | 47.4316 | 82.1234 |
| Std. Vap 0° C. (m³/h) | | 10.2403 | 10.2403 | 17.7053 | 17.7053 | 17.7053 | 17.7053 | 17.7053 | 29.5626 |
| Component | Methane | 58.297461 | 58.297461 | 33.717832 | 33.717832 | 33.717832 | 33.717832 | 33.717832 | 0.139371 |
| Mole % | CO₂ | 38.864961 | 38.864961 | 22.478548 | 22.478548 | 22.478548 | 22.478548 | 22.478548 | 6.146172 |
| | Water | 2.339214 | 2.339214 | 43.515378 | 43.515378 | 43.515378 | 43.515378 | 43.515378 | 13.323644 |
| | CO | 0.000000 | 0.000000 | 0.000000 | 0.000000 | 0.000000 | 0.000000 | 0.000000 | 27.370977 |
| | Hydrogen | 0.000000 | 0.000000 | 0.000000 | 0.000000 | 0.000000 | 0.000000 | 0.000000 | 52.857201 |
| | Methanol | 0.000000 | 0.000000 | 0.000000 | 0.000000 | 0.000000 | 0.000000 | 0.000000 | 0.000000 |
| | Nitrogen | 0.498365 | 0.498365 | 0.288242 | 0.288242 | 0.288242 | 0.288242 | 0.288242 | 0.172631 |

| Stream # | 111 | 112 | 113 | 120 | 123 | 124 | 125 | 130 |
|---|---|---|---|---|---|---|---|---|
| Stream Name | second exchange discharge line | fourth continuing line | first gas stream | fifth continuing line | second transport discharge stream | sixth continuing line | second gas stream | third gas stream |
| Molar Flow (kmol/h) | 1.3190 | 1.3190 | 1.1562 | 1.5712 | 1.5712 | 1.5712 | 1.5616 | 1.5584 |
| Mass Flow (kmol/h) | 18.3438 | 18.3438 | 15.4120 | 19.9716 | 19.9716 | 19.9716 | 19.7979 | 19.7402 |
| Temp. (° C.) | 220.9568 | 20.000 | 19.7698 | 19.1200 | 272.1195 | 20.00 | 19.9811 | 4.9957 |
| Pressure (bar) | 1.5000 | 1.5000 | 1.4500 | 1.4500 | 8.0000 | 7.9500 | 7.9000 | 49.9000 |
| Vapor Mole Fraction | 1.000 | 0.8764 | 1.000 | 1.000 | 1.000 | 0.9939 | 1.000 | 1.000 |
| Enth (kW) | −29.597 | −33.855 | −20.908 | −24.592 | −21.270 | −24.706 | −23.940 | −23.963 |
| Actual Volume (m³/h) | 36.1304 | 18.7887 | 19.4221 | 26.3372 | 89.9313 | 4.7972 | 4.8270 | 0.7323 |

37      38

TABLE 1-continued

| | | | | | | | | |
|---|---|---|---|---|---|---|---|---|
| Std. Vap 0° C. (m³/h) | | 29.5626 | 29.5626 | 25.9150 | 35.2172 | 35.2172 | 35.2172 | 35.0013 | 34.9301 |
| Component | Methane | 0.139371 | 0.139371 | 0.158987 | 0.413004 | 0.413004 | 0.413004 | 0.415551 | 0.416398 |
| Mole % | $CO_2$ | 6.146172 | 6.146172 | 7.011187 | 5.243682 | 5.243673 | 5.243673 | 5.276002 | 5.286727 |
| | Water | 13.323644 | 13.323644 | 1.123721 | 0.826994 | 0.826993 | 0.826993 | 0.215995 | 0.015039 |
| | CO | 27.370977 | 27.370977 | 31.223544 | 29.915914 | 29.915863 | 29.915863 | 30.100390 | 30.161741 |
| | Hydrogen | 52.857201 | 52.857201 | 60.285640 | 61.588317 | 61.588383 | 61.588383 | 61.968279 | 62.094581 |
| | Methanol | 0.000000 | 0.000000 | 0.000000 | 0.077852 | 0.077853 | 0.077853 | 0.077622 | 0.075392 |
| | Nitrogen | 0.172631 | 0.172631 | 0.196929 | 1.934231 | 1.934228 | 1.934228 | 1.946159 | 1.950125 |

| Stream # | | 131 | 132 | 133 | 134 | 135 | 136 | 137 | 138 |
|---|---|---|---|---|---|---|---|---|---|
| Stream Name | | wash process stream discharge line | third exchange discharge line | first methanol reactor discharge line | fourth exchange discharge line | ninth continuing line | fourth gas stream | fifth exchange discharge line | tenth continuing line |
| Molar Flow (kmol/h) | | 1.4403 | 1.4403 | 0.9936 | 0.9936 | 0.9936 | 0.7599 | 0.7599 | 0.7599 |
| Mass Flow (kmol/h) | | 15.7546 | 15.7546 | 15.7546 | 15.7549 | 15.7549 | 8.2746 | 8.2746 | 8.2746 |
| Temp. (° C.) | | 39.3707 | 200.0000 | 225.0000 | 113.8260 | 20.0000 | 19.9978 | 200.0000 | 200.0013 |
| Pressure (bar) | | 49.9000 | 49.8000 | 49.7500 | 49.6500 | 49.6500 | 49.6000 | 49.500 | 49.4000 |
| Vapor Mole Fraction | | 1.000 | 1.000 | 1.000 | 0.8796 | 0.7647 | 1.000 | 1.000 | 1.000 |
| Enth (kW) | | −14.554 | −12.631 | −18.949 | −20.871 | −22.818 | −7.2958 | −6.1617 | −6.1617 |
| Actual Volume (m³/h) | | 0.7663 | 1.1628 | 0.8313 | 0.5751 | 0.3903 | 0.3813 | 0.6171 | 0.6184 |
| Std. Vap 0° C. (m³/h) | | 32.2826 | 32.2826 | 22.2700 | 22.2712 | 22.2712 | 17.0312 | 17.0312 | 17.0312 |
| Component | Methane | 0.334781 | 0.334781 | 0.485298 | 0.485304 | 0.485304 | 0.629210 | 0.629210 | 0.629210 |
| Mole % | $CO_2$ | 0.146369 | 0.146369 | 0.191305 | 0.191311 | 0.191311 | 0.220662 | 0.220662 | 0.220662 |
| | Water | 0.001195 | 0.001195 | 0.022604 | 0.022604 | 0.022604 | 0.000218 | 0.000218 | 0.000218 |
| | CO | 30.986148 | 30.986148 | 22.458407 | 22.457303 | 22.457303 | 29.323220 | 29.323220 | 29.323220 |
| | Hydrogen | 65.734816 | 65.734816 | 50.308353 | 50.310498 | 50.310498 | 65.754080 | 65.754080 | 65.754080 |
| | Methanol | 0.799273 | 0.799273 | 23.638596 | 23.637435 | 23.637435 | 0.292072 | 0.292072 | 0.292072 |
| | Nitrogen | 1.997406 | 1.997406 | 2.895438 | 2.895541 | 2.895541 | 3.780542 | 3.780542 | 3.780542 |

| Stream # | | 139 | 140 | 141 | 142 | 143 | 144 | 146 | 160 |
|---|---|---|---|---|---|---|---|---|---|
| Stream Name | | second methanol reactor discharge line | sixth exchange discharge line | eleventh continuing line | fifth gas stream | twelfth continuing line | thirteenth continuing line | fifteenth continuing line | $CO_2$-methanol line |
| Molar Flow (kmol/h) | | 0.5367 | 0.5367 | 0.5367 | 0.4235 | 0.0085 | 0.0085 | 0.4150 | 12.6109 |
| Mass Flow (kmol/h) | | 8.2746 | 8.2746 | 8.2746 | 4.6527 | 0.0931 | 0.0931 | 4.5596 | 403.9856 |
| Temp. (° C.) | | 225.0000 | 102.7713 | 20.0000 | 19.9979 | 19.9979 | 17.2308 | 19.9979 | 37.6008 |
| Pressure (bar) | | 49.3500 | 49.2500 | 49.2000 | 49.1500 | 49.1500 | 1.0000 | 49.1500 | 49.9000 |
| Vapor Mole Fraction | | 1.000 | 0.8701 | 0.7891 | 1.000 | 1.00 | 1.000 | 1.000 | 0.0000 |
| Enth (kW) | | −9.3067 | −10.441 | −11.278 | −3.7596 | −0.75192 | −0.075192 | −3.6844 | −834.99 |
| Actual Volume (m³/h) | | 0.4538 | 0.3027 | 0.2187 | 0.2143 | 0.0043 | 0.2045 | 0.2100 | 0.5257 |
| Std. Vap 0° C. (m³/h) | | 12.0296 | 12.0296 | 12.0296 | 9.4920 | 0.1898 | 0.1898 | 9.3022 | 282.6554 |
| Component | Methane | 0.890821 | 0.890819 | 0.890819 | 1.120670 | 1.120670 | 1.120670 | 1.120670 | 0.013255 |
| Mole % | $CO_2$ | 0.281229 | 0.281228 | 0.281228 | 0.319585 | 0.319585 | 0.319585 | 0.319585 | 0.667030 |
| | Water | 0.031488 | 0.031487 | 0.031487 | 0.000341 | 0.000341 | 0.000341 | 0.000341 | 0.192376 |
| | CO | 20.757493 | 20.757452 | 20.757452 | 26.272988 | 26.272991 | 26.272991 | 26.272991 | 0.188645 |
| | Hydrogen | 51.484269 | 51.484370 | 51.484370 | 65.217483 | 65.217483 | 65.217483 | 65.217483 | 0.166087 |
| | Methanol | 21.202305 | 21.202262 | 21.202262 | 0.294742 | 0.294742 | 0.294742 | 0.294742 | 98.759729 |
| | Nitrogen | 5.352400 | 5.352383 | 5.352383 | 6.774185 | 6.774185 | 6.774185 | 6.774185 | 0.012880 |

| Stream # | | 161 | 162 | 163 | 164 | 165 | 170 | 171 | 173 |
|---|---|---|---|---|---|---|---|---|---|
| Stream Name | | sixteenth continuing line | fourth liquid stream | seventeenth continuing line | fifth liquid stream | eighteenth continuing line | first flash column discharge line | first vent stream | nineteenth continuing line |
| Molar Flow (kmol/h) | | 12.6109 | 0.2338 | 0.2338 | 0.1132 | 0.1132 | 12.7969 | 0.1609 | 0.1609 |
| Mass Flow (kmol/h) | | 403.9856 | 7.4803 | 7.4803 | 3.6220 | 3.6220 | 409.7397 | 5.3481 | 5.3481 |
| Temp. (° C.) | | 37.4445 | 19.9978 | 20.0083 | 19.9979 | 20.0443 | 36.0019 | 36.0019 | 36.0019 |
| Pressure (bar) | | 1.5000 | 49.6000 | 1.5000 | 49.1500 | 1.5000 | 1.5000 | 1.5000 | 1.5000 |
| Vapor Mole Fraction | | 0.007895 | 0.0000 | 0.003209 | 0.0000 | 0.003390 | 0.0000 | 1.000 | 1.000 |
| Enth (kW) | | −834.99 | 15.522 | −15.522 | −7.5186 | −7.5186 | −846.69 | −11.335 | −11.335 |
| Actual Volume (m³/h) | | 2.2236 | 0.0095 | 0.003209 | 0.0046 | 0.0108 | 0.5261 | 2.7390 | 2.7390 |
| Std. Vap 0° C. (m³/h) | | 282.6554 | 5.2400 | 5.2400 | 2.5376 | 2.5376 | 286.8259 | 3.6071 | 3.6071 |
| Component | Methane | 0.013255 | 0.017581 | 0.017581 | 0.031031 | 0.031031 | 0.000033 | 1.083395 | 1.083395 |
| Mole % | $CO_2$ | 0.667030 | 0.095912 | 0.095912 | 0.137750 | 0.137750 | 0.030707 | 50.063747 | 50.063747 |
| | Water | 0.192376 | 0.095354 | 0.095354 | 0.147993 | 0.147993 | 0.192446 | 0.014708 | 0.014708 |
| | CO | 0.188645 | 0.141742 | 0.141742 | 0.125899 | 0.125899 | 0.000293 | 15.053664 | 15.053664 |
| | Hydrogen | 0.166087 | 0.115872 | 0.115872 | 0.113944 | 0.113944 | 0.000235 | 13.244642 | 13.244642 |
| | Methanol | 98.759729 | 99.514413 | 99.514413 | 99.409425 | 99.409425 | 99.776274 | 19.490014 | 19.490014 |
| | Nitrogen | 0.012880 | 0.019118 | 0.019118 | 0.33958 | 0.33958 | 0.000015 | 1.059830 | 1.059830 |

TABLE 1-continued

| Stream # | 174 | 175 | 176 | 177 | 178 | 179 | 180 |
|---|---|---|---|---|---|---|---|
| Stream Name | twentieth continuing line | second vent stream | second flash column discharge line | twenty-first continuing line | methanol product recovery stream | second inlet liquid line | methanol recycle stream |
| Molar Flow (kmol/h) | 0.1609 | 0.1349 | 0.0260 | 0.3042 | 0.3302 | 12.4927 | 12.4927 |
| Mass Flow (kmol/h) | 5.3481 | 4.5107 | 0.8374 | 9.7397 | 10.5771 | 400.000 | 400.0000 |
| Temp. (° C.) | 5.000 | 1.6395 | 1.6395 | 36.0019 | 33.4310 | 36.0019 | 39.3950 |
| Pressure (bar) | 1.1000 | 1.0000 | 1.0000 | 1.5000 | 1.0000 | 1.500 | 50.0000 |
| Vapor Mole Fraction | 0.8358 | 1.000 | 0.0000 | 0.0000 | 0.0000 | 0.0000 | 0.0000 |
| Enth (kW) | −11.656 | −9.8979 | −1.7578 | −20.126 | −21.884 | −826.57 | −825.58 |
| Actual Volume (m³/h) | 2.8174 | 3.0710 | 0.0010 | 0.0125 | 0.0136 | 0.5136 | 0.5158 |
| Std. Vap 0° C. (m³/h) | 3.6071 | 3.0247 | 0.5824 | 6.8180 | 7.4004 | 280.0079 | 280.0079 |
| Component Methane | 1.083395 | 1.291993 | 0.000055 | 0.000033 | 0.000035 | 0.000033 | 0.000033 |
| Mole %    $CO_2$ | 50.063747 | 59.389198 | 1.632829 | 0.030707 | 0.156793 | 0.030707 | 0.030707 |
| Water | 0.014708 | 0.001175 | 0.084993 | 0.192446 | 0.183993 | 0.192446 | 0.192446 |
| CO | 15.053664 | 17.952183 | 0.000461 | 0.000293 | 0.000306 | 0.000293 | 0.000293 |
| Hydrogen | 13.244642 | 15.7948867 | 0.000269 | 0.000235 | 0.000237 | 0.000235 | 0.000235 |
| Methanol | 19.490014 | 4.306675 | 98.281366 | 99.776274 | 99.658620 | 99.776274 | 99.776274 |
| Nitrogen | 1.059830 | 1.263897 | 0.000024 | 0.000014 | 0.000015 | 0.000014 | 0.000014 |

Example 2

Example 2 is a biomethanol production system 410 configured as shown in FIG. 5. The parameters and content of the various streams is provided below in Table 2. The biomethanol production system 410 is configured to operate in two different modes. In the first mode, hydrogen is fed downstream of the reformer reactor 12 to convert excess carbon dioxide to methanol directly. In the first mode, the methanol wash is not operated. In the second mode, the methanol wash is in operation, and no hydrogen is added downstream of the reformer reactor 12. During the operation of Example 2, the biomethanol production system 410 is operating in the second mode. Thus, the hydrogen feed line 121 has no flow in Example 2.

The carbon dioxide recycle line 172 has no flow in Example 2. However, it is understood that the carbon dioxide recycle line 172 may be used to take unreacted methane back to the reformer reactor 12. The second vent stream 175 is a purge line that may be vented through a flare. The first liquid stream 210, the second liquid stream 211, and the third liquid stream 212 contain surplus water from the system, and the contents of the liquid streams 210, 211, 212 are discarded.

The reformer reactor 12 of Example 2 is operated at a temperature of 850° C. (1123.15° K), has a heat duty of 17.2212 kW, and an overall heat of reaction of 15.4943 kW. The methanol reactor 14a of Example 2 is operated at a temperature of 225° C. (498.15° K) and has a heat duty of −5.3516 kW. The methanol reactor 14b of Example 1 is operated at a temperature of 225° C. (498.15° K) and has a heat duty of −2.6365 kW.

TABLE 2

| Stream # | 101 | 102 | 103 | 104 | 105 | 107 | 110 | 111 |
|---|---|---|---|---|---|---|---|---|
| Stream Name | inlet gas line | feed gas line | first continuing line | second continuing line | third continuing line | first exchange discharge line | reformer discharge line | second exchange discharge line |
| Molar Flow (kmol/h) | 0.4574 | 0.4574 | 0.7849 | 0.7849 | 0.7849 | 0.7849 | 1.2903 | 1.2903 |
| Mass Flow (kmol/h) | 12.3735 | 12.3735 | 18.2735 | 18.2735 | 18.2735 | 18.2735 | 18.2733 | 18.2733 |
| Temp. (° C.) | 20.0000 | 57.5771 | 98.7610 | 98.7610 | 98.7610 | 810.0000 | 850.0000 | 232.2068 |
| Pressure (bar) | 1.0000 | 1.5000 | 1.5000 | 1.5000 | 1.5000 | 1.5000 | 1.5000 | 1.5000 |
| Vapor Mole Fraction | 1.000 | 1.000 | 1.000 | 1.000 | 1.000 | 1.000 | 1.000 | 1.000 |
| Enth (kW) | −24.564 | −24.391 | −45.993 | −45.993 | −45.993 | −38.692 | −21.471 | −28.772 |
| Actual Volume (m³/h) | 11.1140 | 8.3613 | 16.0933 | 16.0933 | 16.0933 | 47.1291 | 80.3365 | 36.1486 |
| Std. Vap 0° C. (m³/h) | 10.2514 | 10.2514 | 17.5920 | 17.5920 | 17.5920 | 17.5920 | 28.9193 | 28.9193 |
| Flow    Methane | 4.0797 | 4.0797 | 4.0797 | 4.0797 | 4.0797 | 4.0797 | 0.0259 | 0.0259 |
| Rate    $CO_2$ | 7.4612 | 7.4612 | 7.4612 | 7.4612 | 7.4612 | 7.4612 | 3.5162 | 3.5162 |
| (kg/hour)    Water | 0.1927 | 0.1927 | 6.0927 | 6.0927 | 6.0927 | 6.0927 | 3.1554 | 3.1554 |
| CO | 0.0000 | 0.0000 | 0.0000 | 0.0000 | 0.0000 | 0.0000 | 9.5886 | 9.5886 |
| Hydrogen | 0.0000 | 0.0000 | 0.0000 | 0.0000 | 0.0000 | 0.0000 | 1.3474 | 1.3474 |
| Methanol | 0.0000 | 0.0000 | 0.0000 | 0.0000 | 0.0000 | 0.0000 | 0.0000 | 0.0000 |
| Nitrogen | 0.6399 | 0.6399 | 0.6399 | 0.6399 | 0.6399 | 0.6399 | 0.6399 | 0.6399 |

| Stream # | 112 | 113 | 114 | 120 | 123 | 124 | 125 | 126 |
|---|---|---|---|---|---|---|---|---|
| Stream Name | fourth continuing line | first gas stream | twenty-second continuing line | fifth continuing line | second transport discharge stream | sixth continuing line | second gas stream | seventh continuing line |
| Molar Flow (kmol/h) | 1.2903 | 1.1326 | 1.1326 | 1.6867 | 1.6867 | 1.6867 | 1.6736 | 1.6736 |
| Mass Flow (kmol/h) | 18.2733 | 15.4321 | 15.4321 | 22.7827 | 22.7827 | 22.7827 | 22.5389 | 22.5389 |
| Temp. (° C.) | 20.0000 | 19.7197 | 19.7196 | 18.8025 | 271.7162 | 20.0000 | 19.9749 | 300.5915 |
| Pressure (bar) | 1.5000 | 1.4500 | 1.4500 | 1.4500 | 8.0000 | 7.9500 | 7.9000 | 50.0000 |
| Vapor Mole Fraction | 0.8776 | 1.000 | 1.000 | 1.000 | 1.000 | 0.9922 | 1.000 | 1.000 |

TABLE 2-continued

| | | | | | | | | |
|---|---|---|---|---|---|---|---|---|
| Enth (kW) | −33.047 | −20.501 | −20.501 | −23.828 | −20.266 | −23.980 | −22.940 | −18.990 |
| Actual Volume (m³/h) | 18.4027 | 19.0207 | 19.0207 | 28.2420 | 9.5810 | 5.1417 | 5.1735 | 1.6287 |
| Std. Vap 0° C. (m³/h) | 28.9193 | 25.3848 | 25.3848 | 37.8055 | 37.8055 | 37.8055 | 37.5107 | 37.5107 |
| Flow Rate (kg/hour) Methane | 0.0259 | 0.0259 | 0.0259 | 0.0848 | 0.0848 | 0.0848 | 0.0848 | 0.0848 |
| CO₂ | 3.5162 | 3.5157 | 3.5157 | 3.7035 | 3.7035 | 3.7035 | 3.7033 | 3.7033 |
| Water | 3.1554 | 0.3147 | 0.3147 | 0.3148 | 0.3148 | 0.3148 | 0.0867 | 0.0867 |
| CO | 9.5886 | 9.5886 | 9.5886 | 11.9786 | 11.9786 | 11.9786 | 11.9786 | 11.9786 |
| Hydrogen | 1.3474 | 1.3474 | 1.3474 | 1.9837 | 1.9837 | 1.9837 | 1.9837 | 1.9837 |
| Methanol | 0.0000 | 0.0000 | 0.0000 | 0.0726 | 0.0726 | 0.0726 | 0.0570 | 0.0570 |
| Nitrogen | 0.6399 | 0.6399 | 0.6399 | 4.6446 | 4.6446 | 4.6446 | 4.6446 | 4.6446 |

| Stream # | 127 | 130 | 131 | 132 | 133 | 134 | 135 | 136 |
|---|---|---|---|---|---|---|---|---|
| Stream Name | eighth continuing line | third gas stream | wash process stream discharge line | third exchange discharge line | first methanol reactor discharge line | fourth exchange discharge line | ninth continuing line | fourth gas stream |
| Molar Flow (kmol/h) | 1.6736 | 1.6680 | 1.4890 | 1.4890 | 1.1064 | 1.1064 | 1.1064 | 0.9052 |
| Mass Flow (kmol/h) | 22.5389 | 22.4245 | 17.7131 | 17.7131 | 17.7132 | 17.7132 | 17.7132 | 11.2998 |
| Temp. (° C.) | 5.0000 | 4.9961 | 32.2548 | 200.0000 | 225.0000 | 102.0018 | 20.0000 | 19.9974 |
| Pressure (bar) | 49.9500 | 49.9000 | 49.9000 | 49.8000 | 49.7500 | 49.6500 | 49.6500 | 49.6000 |
| Vapor Mole Fraction | 0.9967 | 1.000 | 1.000 | 1.000 | 1.000 | 0.9000 | 0.8181 | 1.000 |
| Enth (kW) | −23.259 | −22.830 | −13.081 | −11.005 | −16.357 | −18.433 | −20.106 | −6.7940 |
| Actual Volume (m³/h) | 0.7839 | 0.7845 | 0.7739 | 1.2018 | 0.9200 | 0.6362 | 0.4620 | 0.4543 |
| Std. Vap 0° C. (m³/h) | 37.5107 | 37.3868 | 33.3734 | 33.3734 | 24.7982 | 24.7981 | 24.7981 | 20.2882 |
| Flow Rate (kg/hour) Methane | 0.0848 | 0.0848 | 0.0663 | 0.0663 | 0.0663 | 0.0663 | 0.0663 | 0.0659 |
| CO₂ | 3.7033 | 3.7022 | 0.2914 | 0.2914 | 0.2624 | 0.2624 | 0.2624 | 0.2442 |
| Water | 0.0867 | 0.0057 | 0.0002 | 0.0002 | 0.0121 | 0.0121 | 0.0121 | 0.0000 |
| CO | 11.9786 | 11.9786 | 10.6792 | 10.6792 | 5.3395 | 5.3395 | 5.3395 | 5.3229 |
| Hydrogen | 1.9837 | 1.9837 | 1.8684 | 1.8684 | 1.0959 | 1.0959 | 1.0959 | 1.0941 |
| Methanol | 0.0570 | 0.0247 | 0.3479 | 0.3479 | 6.4774 | 6.4773 | 6.4773 | 0.1186 |
| Nitrogen | 4.6446 | 4.6446 | 4.4595 | 4.4595 | 4.4595 | 4.4595 | 4.4595 | 4.4540 |

| Stream # | 137 | 139 | 140 | 141 | 142 | 143 | 280 | 146 |
|---|---|---|---|---|---|---|---|---|
| Stream Name | fifth exchange discharge line | second methanol reactor discharge line | sixth exchange discharge line | eleventh continuing line | fifth gas stream | twelfth continuing line | nitrogen discharge line | fifteenth continuing line |
| Molar Flow (kmol/h) | 0.9052 | 0.7140 | 0.7140 | 0.7140 | 0.6157 | 0.0000 | 0.0616 | 0.5542 |
| Mass Flow (kmol/h) | 11.2998 | 11.2998 | 11.2998 | 11.2995 | 8.1673 | 0.0000 | 0.8167 | 7.3506 |
| Temp. (° C.) | 200.0000 | 225.0000 | 87.3692 | 20.0000 | 19.9972 | 0.0000 | 16.9149 | 19.9972 |
| Pressure (bar) | 49.5000 | 49.4500 | 49.3500 | 49.3000 | 49.2500 | 0.0000 | 1.5000 | 49.2500 |
| Vapor Mole Fraction | 1.000 | 1.000 | 0.9137 | 0.8623 | 1.000 | 0.0000 | 1.000 | 1.000 |
| Enth (kW) | −5.4408 | −8.0774 | −9.4305 | −10.208 | −3.6967 | 0.0000 | −0.36967 | −3.3270 |
| Actual Volume (m³/h) | 0.7352 | 0.6008 | 0.4052 | 0.3149 | 0.3112 | 0.0000 | 0.9904 | 0.2801 |
| Std. Vap 0° C. (m³/h) | 20.2882 | 16.0039 | 16.0038 | 16.0045 | 13.8007 | 0.0000 | 1.3801 | 12.4206 |
| Flow Rate (kg/hour) Methane | 0.0659 | 0.0659 | 0.0659 | 0.0659 | 0.0655 | 0.0000 | 0.0066 | 0.0590 |
| CO₂ | 0.2442 | 0.2198 | 0.2198 | 0.2198 | 0.2087 | 0.0000 | 0.0209 | 0.1878 |
| Water | 0.0000 | 0.0100 | 0.0100 | 0.0100 | 0.0000 | 0.0000 | 0.0000 | 0.0000 |
| CO | 5.3229 | 2.6614 | 2.6614 | 2.6614 | 2.6556 | 0.0000 | 0.2656 | 2.3900 |
| Hydrogen | 1.0941 | 0.7077 | 0.7077 | 0.7078 | 0.7070 | 0.0000 | 0.0707 | 0.6363 |
| Methanol | 0.1186 | 3.1810 | 3.1810 | 3.1810 | 0.0807 | 0.0000 | 0.0081 | 0.0726 |
| Nitrogen | 4.4540 | 4.4540 | 4.4539 | 4.4536 | 4.4497 | 0.0000 | 0.4450 | 4.0047 |

| Stream # | 160 | 161 | 162 | 163 | 164 | 165 | 231 | 260 |
|---|---|---|---|---|---|---|---|---|
| Stream Name | CO₂-methanol line | sixteenth continuing line | fourth liquid stream | seventeenth continuing line | fifth liquid stream | eighteenth continuing line | second CO₂-methanol line | wash discharge line |
| Molar Flow (kmol/h) | 12.6929 | 12.6929 | 0.2012 | 0.2012 | 0.0983 | 0.0983 | 0.2962 | 12.7579 |
| Mass Flow (kmol/h) | 404.7114 | 404.7114 | 6.4134 | 6.4134 | 3.1322 | 3.1322 | 7.2744 | 407.7996 |
| Temp. (° C.) | 30.6631 | 29.9746 | 19.9974 | 19.7743 | 19.9972 | 19.8241 | 29.7242 | 28.9614 |
| Pressure (bar) | 49.9000 | 1.5000 | 49.6000 | 1.5000 | 49.2500 | 1.5000 | 1.5000 | 1.5000 |
| Vapor Mole Fraction | 0.0000 | 0.01530 | 0.0000 | 0.009907 | 0.0000 | 0.009465 | 1.000 | 0.0000 |
| Enth (kW) | −839.63 | −839.63 | −13.312 | −13.312 | −6.5117 | −6.5117 | −12.762 | −847.06 |
| Actual Volume (m³/h) | 0.5246 | 3.7606 | 0.0082 | 0.0403 | 0.0040 | 0.0190 | 4.9548 | 0.5189 |
| Std. Vap 0° C. (m³/h) | 284.4949 | 284.4949 | 4.5099 | 4.5099 | 2.2038 | 2.2038 | 6.6382 | 285.9506 |
| Flow Rate (kg/hour) Methane | 0.0195 | 0.0195 | 0.0005 | 0.0005 | 0.0003 | 0.0003 | 0.0258 | 0.0010 |
| CO₂ | 3.8869 | 3.8869 | 0.0182 | 0.0182 | 0.0111 | 0.0111 | 3.4518 | 0.4854 |
| Water | 1.3611 | 1.3611 | 0.0121 | 0.0121 | 0.0100 | 0.0100 | 0.0011 | 1.3821 |
| CO | 1.3180 | 1.3180 | 0.0166 | 0.0166 | 0.0058 | 0.0058 | 1.5871 | 0.0189 |
| Hydrogen | 0.1178 | 0.1178 | 0.0017 | 0.0017 | 0.0008 | 0.0008 | 0.1885 | 0.0026 |
| Methanol | 397.8111 | 397.8111 | 6.3587 | 6.3587 | 3.1003 | 3.1003 | 1.3809 | 405.8975 |
| Nitrogen | 0.1969 | 0.1969 | 0.0056 | 0.0056 | 0.0039 | 0.0039 | 0.6393 | 0.0121 |

TABLE 2-continued

| Stream # | 173 | 174 | 175 | 176 | 177 | 178 | 179 | 180 |
|---|---|---|---|---|---|---|---|---|
| Stream Name | nineteenth continuing line | twentieth continuing line | second vent stream | second flash column discharge line | twenty-first continuing line | methanol product recovery stream | second inlet liquid line | methanol recycle stream |
| Molar Flow (kmol/h) | 0.2962 | 0.2962 | 0.2677 | 0.0285 | 0.2440 | 0.2725 | 12.5139 | 12.5139 |
| Mass Flow (kmol/h) | 7.2744 | 7.2744 | 6.3606 | 0.9139 | 7.7996 | 8.7135 | 400.0000 | 400.0000 |
| Temp. (° C.) | 29.7242 | 5.0000 | 5.0001 | 5.0001 | 28.9614 | 26.4958 | 28.9614 | 32.3709 |
| Pressure (bar) | 1.5000 | 1.0000 | 1.0000 | 1.0000 | 1.5000 | 1.0000 | 1.5000 | 50.0000 |
| Vapor Mole Fraction | 1.000 | 0.9037 | 1.000 | 0.0000 | 0.0000 | 0.0001057 | 0.0000 | 0.0000 |
| Enth (kW) | −12.762 | −13.122 | −11.212 | −1.9098 | −16.201 | −18.111 | −830.86 | −829.88 |
| Actual Volume (m³/h) | 4.9548 | 6.1800 | 6.1789 | 0.0011 | 0.0099 | 0.0118 | 0.5090 | 0.5114 |
| Std. Vap 0° C. (m³/h) | 6.6382 | 6.6382 | 5.9991 | 0.6391 | 5.4691 | 6.1082 | 280.4815 | 280.4815 |
| Flow Rate Methane | 0.0258 | 0.0258 | 0.0258 | 0.0000 | 0.0000 | 0.0000 | 0.0010 | 0.0010 |
| (kg/hour) CO₂ | 3.4518 | 3.4518 | 3.4479 | 0.0039 | 0.0093 | 0.0132 | 0.4761 | 0.4761 |
| Water | 0.0011 | 0.0011 | 0.0001 | 0.0010 | 0.0264 | 0.0274 | 1.3556 | 1.3556 |
| CO | 1.5871 | 1.5871 | 1.5870 | 0.0001 | 0.0004 | 0.0004 | 0.0185 | 0.0185 |
| Hydrogen | 0.1885 | 0.1885 | 0.1884 | 0.0000 | 0.0000 | 0.0001 | 0.0026 | 0.0026 |
| Methanol | 1.3809 | 1.3809 | 0.4720 | 0.9089 | 7.7632 | 8.6722 | 398.1342 | 398.1342 |
| Nitrogen | 0.6393 | 0.6393 | 0.6393 | 0.0000 | 0.0002 | 0.0002 | 0.0119 | 0.0119 |

| Stream # | 201 | 202 | 210 | 211 | 212 |
|---|---|---|---|---|---|
| Stream Name | inlet water line | feed water line | first liquid stream | second liquid stream | third liquid stream |
| Molar Flow (kmol/h) | 0.3275 | 0.3275 | 0.1577 | 0.0132 | 0.0055 |
| Mass Flow (kmol/h) | 5.9000 | 5.9000 | 2.8412 | 0.2439 | 0.1144 |
| Temp. (° C.) | 225.0000 | 163.4439 | 19.7197 | 19.9749 | 4.9961 |
| Pressure (bar) | 25.8247 | 1.5000 | 1.4500 | 7.9000 | 49.9000 |
| Vapor Mole Fraction | 1.000 | 1.000 | 0.0000 | 0.0000 | 0.0000 |
| Enth (kW) | −21.603 | −21.603 | −12.547 | −1.0399 | −0.42913 |
| Actual Volume (m³/h) | 0.4714 | 7.8608 | 0.0028 | 0.0002 | 0.0001 |
| Std. Vap 0° C. (m³/h) | 7.3406 | 7.3406 | 3.5345 | 0.2947 | 0.1239 |
| Flow Rate Methane | 0.0000 | 0.0000 | 0.0000 | 0.0000 | 0.0000 |
| (kg/hour) CO₂ | 0.0000 | 0.0000 | 0.0005 | 0.0002 | 0.0011 |
| Water | 5.9000 | 5.9000 | 2.8407 | 0.2280 | 0.0810 |
| CO | 0.0000 | 0.0000 | 0.0000 | 0.0000 | 0.0000 |
| Hydrogen | 0.0000 | 0.0000 | 0.0000 | 0.0000 | 0.0000 |
| Methanol | 0.0000 | 0.0000 | 0.0000 | 0.0156 | 0.0322 |
| Nitrogen | 0.0000 | 0.0000 | 0.0000 | 0.0000 | 0.0000 |

As shown in Table 2, the first methanol reactor 14a converts (i) about 10% of the carbon dioxide and (ii) about 41% of the hydrogen, based on the total amount of the respective components flowing through the first methanol reactor 14a (in kg/h), into methanol. The second methanol reactor 14b converts (i) about 10% of the carbon dioxide and (ii) about 35% of the hydrogen, based on the total amount of the respective components flowing through the second methanol reactor 14b (in kg/h), into methanol. Further, the biomethanol production system 410 recycles about forty-five times the amount of methanol that is recovered. In other words, the methanol recycle stream 180 contains about 45× the amount of methanol (in kg/h) than the methanol product recovery stream 178.

As shown in Tables 1 and 2, the systems described herein provide significant advantages, including the removal of excess carbon dioxide without requiring the addition of hydrogen to the process stream(s). This increases the efficiency and cost effectiveness of the system compared to the prior art.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A biomethanol production system comprising:
a feed stream comprising methane, water, and carbon dioxide;
a prefilter including an activated carbon filter designed to remove at least one contaminant from the feed stream;
a reformer reactor capable of reacting the feed stream to form a syngas mixture comprising hydrogen, carbon monoxide, and carbon dioxide;
a methanol reactor capable of reacting the syngas mixture to form biomethanol product;
a wash column comprising the syngas mixture and the biomethanol product, wherein the biomethanol product is capable of absorbing carbon dioxide from the syngas mixture;
a flash column comprising a vent capable of venting the absorbed carbon dioxide;
a methanol recycle stream comprising biomethanol discharged from the flash column, wherein the methanol recycle stream places the flash column in fluid communication with the wash column; and
a liquid transport device configured to transport biomethanol in the methanol recycle stream from the flash column to the wash column.

2. The biomethanol production system of claim 1 comprising:

a $CO_2$-methanol line that puts the wash column in fluid communication with the flash column, the $CO_2$-methanol stream comprising the carbon dioxide absorbed in the biomethanol product discharged from the wash column.

3. The biomethanol production system of claim 2, wherein the $CO_2$-methanol line comprises at least 100% more carbon dioxide than the methanol recycle stream, based on the total moles of carbon dioxide contained in the respective stream.

4. The biomethanol production system of claim 2, wherein a ratio of moles of carbon dioxide in the $CO_2$-methanol line to moles of carbon dioxide in the methanol recycle stream is from 1.2:1 to 50:1.

5. The biomethanol production system of claim 1 further comprising:

a wash process stream discharge line that puts the wash column in fluid communication with the methanol reactor, the wash process stream discharge line comprising the syngas mixture discharged from the wash column.

6. The biomethanol production system of claim 5, wherein the wash process stream discharge line comprises at least 50% less carbon dioxide than the syngas mixture formed in the reformer reactor.

7. The biomethanol production system of claim 5, wherein a ratio of moles of carbon dioxide in the syngas mixture formed in the reformer reactor to moles of carbon dioxide in the wash process stream discharge line is from 80:1 to 35:1.

8. The biomethanol production system of claim 1, wherein the wash column is upstream of the methanol reactor.

9. The biomethanol production system of claim 1, wherein the wash column is positioned between a first methanol reactor and a second methanol reactor.

10. A biomethanol production system comprising:

a feed stream;

a prefilter including an activated carbon filter designed to remove a contaminant from the feed stream;

a reformer reactor configured to react the feed stream to create a syngas mixture;

a first methanol reactor configured to react the syngas mixture to form a first biomethanol product;

a wash column configured to absorb carbon dioxide from the syngas mixture, the wash column including a wash column discharge line;

a second methanol reactor configured to react the syngas mixture to form a second biomethanol product, wherein the wash column discharge line puts the wash column in fluid communication with the second methanol reactor;

a device configured to release absorbed carbon dioxide from the first and second biomethanol product and vent the absorbed carbon dioxide from the biomethanol production system; and a biomethanol recycle stream that puts the device in fluid communication with the wash column.

11. The biomethanol production system of claim 10, wherein the device is selected from the group consisting of a high-pressure flash distillation column, a low-pressure flash distillation column, and a flash tank.

12. The biomethanol production system of claim 10, wherein the device comprises a flash column including a vent capable of venting the absorbed carbon dioxide and the methanol recycle stream comprises biomethanol.

13. The biomethanol production system of claim 10 further comprising:

a $CO_2$-methanol line that puts the wash column in fluid communication with the device, the $CO_2$-methanol line comprising the carbon dioxide absorbed in the biomethanol product discharged from the wash column.

14. The biomethanol production system of claim 10 wherein:

the wash process stream discharge line comprises the syngas mixture discharged from the wash column, the wash column discharge line is in fluid communication with the second methanol reactor.

15. The biomethanol production system of claim 1, wherein the liquid transport device comprises a suction side in fluid communication with the flash column and a discharge side in fluid communication with the wash column.

16. The biomethanol production system of claim 1, wherein the liquid transport device comprises a mechanical device designed to adjust the pressure of the fluid in the methanol recycle stream.

17. The biomethanol production system of claim 1, wherein the liquid transport device comprises a pump.

18. A biomethanol production system comprising:

a feed stream comprising biogas;

a prefilter comprising an activated carbon filter designed to remove at least one contaminant from the feed stream;

a reformer reactor configured to react the feed stream to generate a syngas mixture;

a first methanol reactor including a first input line and a first discharge line, the first methanol reactor designed to react the syngas mixture to form a first biomethanol stream, wherein the first biomethanol stream is provided to the first discharge line;

a second methanol reactor including a second input line and a second discharge line, wherein the second methanol reactor is positioned downstream of the first methanol reactor and is designed generate a second biomethanol stream that is provided to the second discharge line;

a wash column in fluid communication with the first discharge line of the first methanol reactor and the second input line of the second methanol reactor, wherein the wash column provides a wash column discharge stream to the second methanol reactor;

a flash column in fluid communication with the wash column and the second methanol reactor, the flash column designed to vent absorbed carbon dioxide to generate a biomethanol product stream;

a methanol recycle line including a methanol recycle stream, wherein the methanol recycle stream comprises a portion of the biomethanol product stream discharged from the flash column, wherein the methanol recycle stream places the flash column in fluid communication with the wash column; and a liquid transport device coupled to the methanol recycle line between the flash column and the wash column.

* * * * *